United States Patent
Bansleben et al.

(10) Patent No.: US 6,410,664 B1
(45) Date of Patent: Jun. 25, 2002

(54) CATALYST COMPOSITIONS AND PROCESSES FOR OLEFIN POLYMERS AND COPOLYMERS

(75) Inventors: Donald Albert Bansleben, Columbia, MD (US); Stefan K. Friedrich, San Gabriel, CA (US); Todd Ross Younkin, Pasadena, CA (US); Robert Howard Grubbs, South Pasadena, CA (US); Chunming Wang, Highland Park, NJ (US); Robert Tan Li, Longview, TX (US)

(73) Assignee: Cryovac, Inc., Duncan, SC (US)

( * ) Notice: Subject to any disclaimer, the term of this patent is extended or adjusted under 35 U.S.C. 154(b) by 0 days.

(21) Appl. No.: 09/007,443

(22) Filed: Jan. 15, 1998

Related U.S. Application Data

(63) Continuation-in-part of application No. 08/822,531, filed on Mar. 24, 1997, now abandoned.

(51) Int. Cl.[7] ............................. C08F 4/602; C08F 4/70
(52) U.S. Cl. ..................... 526/141; 526/161; 526/169.1; 526/172; 526/147; 526/91; 526/129; 526/139; 526/140; 526/142; 526/145; 526/146; 526/281
(58) Field of Search .............................. 526/161, 169.1, 526/172, 141, 147

(56) References Cited

U.S. PATENT DOCUMENTS

| | | | |
|---|---|---|---|
| 3,686,159 A | 8/1972 | Bauer et al. | |
| 4,533,651 A | 8/1985 | Masters et al. | |
| 5,210,360 A | 5/1993 | Wu | |
| 5,282,696 A | 2/1994 | Solomon et al. | |
| 5,539,124 A | 7/1996 | Etherton et al. | |
| 5,977,393 A | * 11/1999 | Grubbs et al. | 556/21 |
| 6,174,975 B1 | * 1/2001 | Johnson et al. | 526/172 |

FOREIGN PATENT DOCUMENTS

| | | |
|---|---|---|
| WO | WO 96/23010 | 8/1996 |
| WO | 98/30609 | * 7/1998 |
| WO | 98-30609 | * 7/1998 |
| WO | 9830609 | 7/1998 |

OTHER PUBLICATIONS

Hawley's Condensed Chemical Dictionary, 13th Edition, John Wiley & Sons, p. 296, 1997.*
Chang, Chemistry, McGraw Hill Publishing, p. 497, 1988.*

* cited by examiner

Primary Examiner—David W. Wu
Assistant Examiner—R. Rabago
(74) Attorney, Agent, or Firm—Howard Troffkin; Dan Ruble

(57) ABSTRACT

The present invention is directed to processes of polymerization of olefins and copolymerization of olefins and functionalized olefins in the presence of certain late transition metal bidentate salicylaldimine chelates represented by the formula:

(I)

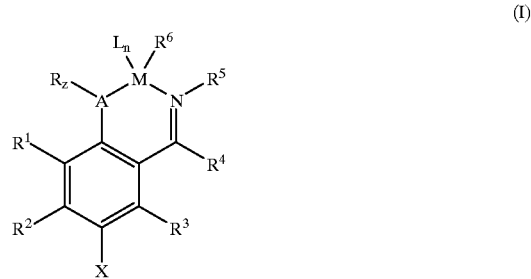

wherein each of the symbols R, $R^1$, $R^2$, $R^3$, $R^4$, $R^5$, $R^6$, L, M, A, X and z are defined within the specification herein below.

160 Claims, No Drawings

CATALYST COMPOSITIONS AND PROCESSES FOR OLEFIN POLYMERS AND COPOLYMERS

This application is a continuation-in-part application of U.S. application Ser. No. 08/822,531, filed Mar. 24, 1997, now abandoned, which is incorporated herein in its entirety by reference.

This invention was made with United States Government support under Contract No. 70NANB5H1136 awarded by the Department of Commerce's National Institute of Standards and Technology. The United States has certain rights in the invention.

The present invention is directed to organometallic catalysts and catalyst compositions useful in the polymerization of alpha-olefins alone or in combination with functionalized olefins, certain bidentate ligand compounds useful in providing the subject catalysts, processes of forming the bidentate ligand compounds and catalysts therefrom, processes of forming olefin oligomers and polymers utilizing the subject catalysts and catalyst compositions, and the oligomers and polymers formed therefrom.

The polyolefin industry has relied on various catalyst and initiator systems. The polymerization of ethylene and other non-polar 1-olefins has been commonly accomplished using organometallic Ziegler-Natta coordination-type catalysts, chromium catalysts, other early transition metal catalysts, as well as free-radical type initiators. Although the array of catalysts available provides different approaches to the manufacture of polyolefins with differing physical and mechanical properties, these catalysts are highly susceptible to a range of substances which poison or deactivate the catalyst's activity. It is well known that even trace amounts of oxygen, carbon monoxide, acetylene or water cause deactivation. Further, catalyst deactivation is caused by organic compounds having oxygen donor groups such as ethers, esters, alcohols, or ketones. Industrial application of these organometallic catalysts requires careful and elaborate measures to assure the absence of such poisons. Because these catalysts are easily poisoned, they tend to form low molecular weight materials, can not be used to provide copolymerization of ethylene with an oxygenated functional monomer, such as an ester, acid or ether functionalized olefin, and generally may produce highly branched polymer products.

More recently, olefin polymerization catalysts have been developed which are less oxophilic than the early transition metal counterparts. For example, U.S. Pat. Nos. 4,310,716; 4,382,153; 4,293,727; 4,301,318; and 4,293,502 each disclose late transition metal (e.g. Ni) complexes which provide low molecular weight oligomers of ethylene. Further, polymerization of ethylene has been successfully shown using complexes based on phosphorous ylide ligands in U.S. Pat. No. 4,537,982 as well as in U.S. Pat. Nos. 4,698,403; 4,716,205; and 4,906,754. These nickel based catalysts formed from P—O bidentate ligands have been shown to provide high activity in the oligomerization and polymerization of ethylene. Still more recently, L. K. Johnson et al in J. Am. Chem. Soc. 1995 117, 6414, reported the formation and use of Pd(II) and Ni(II) based cationic complexes formed from diimine ligands to provide high molecular weight polyolefins. Finally, WO 96/23010 describes a process for the polymerization of olefins using a variety of transition metal complexes of certain diimine bidentate ligands. In many cases the polymerizations provided highly branched polyolefins and were not shown to be useful in providing functionalized copolymer products. Further, in those instances where functionalized copolymers were formed, it was shown that the functional groups reside exclusively at the end of chain branches.

Certain processes and cationic nickel (II) catalyst compositions have been described also by L. K. Johnson et al in WO 97/02298. These cationic complexes are described as active for the polymerization of ethylene and other olefins. They require use of an acid of a non-coordinating monoanion, or some combination of compounds that will generate such acid, in order for the catalyst composition to be rendered active towards olefin polymerization. The present neutral complexes, as well as the use of a Lewis base is not suggested by Johnson et al.

Although Löfgren et al, in Macromolecules 1997, 30, 171–175 describe polymerization of ethylene by cationic zirconium salen bis-chloride complexes with or without a Lewis base (tetrahydrofuran), they show that the catalyst composition exhibits only low levels of activity. There are many references describing the deleterious effect of Lewis base toward late transition metal catalyst compositions as well as single-site catalyst compositions of the metallocene type. For example, EP 94/304642 and EP 94/630910 disclose that Lewis base, such as dialkyl ether, substantially terminates olefin polymerization by a single-site catalyst composition composed of a metallocene compound and partially hydrolyzed aluminum alkyl compound (aluminoxane). Additionally, U.S. Pat. No. 5,571,881 and WO 95/14048 indicate that an unsaturated Lewis base, e.g., vinyl ether, either reacts with the cationic late transition metal catalysts to destroy their activity or causes reduction of the resultant polymer molecular weight.

It is highly desired to provide a catalyst for the oligomerization and polymerization of olefins, in particular ethylene, which provides a substantially linear (low degree of branching) product. It is also highly desired to provide a nonionic catalyst which can provide the linear polymer product. It is still further desired to provide a nonionic catalyst which is capable of providing a product of high molecular weight which is substantially linear and, optionally, which is capable of promoting copolymerization of olefin and functionalized olefin monomer units.

Finally, it is desired to provide a catalyst composition composed of a non-ionic catalyst in combination with an adjunct agent and/or a Lewis base which is capable of providing a product of high molecular weight which is substantially linear and, optionally, which is capable of promoting copolymerization of olefin and functionalized olefin monomer units.

SUMMARY OF THE INVENTION

The present invention is directed to certain late transition metal salicylaldimine chelates as olefin polymerization catalysts, to bidentate ligand compounds of substituted salicylaldimine which are precursors for said catalysts, to catalyst compositions composed of said salicylaldimine chelates in combination with an adjunct agent and/or a Lewis base, the methods of forming said precursor compounds and said catalysts, and the method of polymerizing olefin monomers, especially ethylene, as well as copolymerization of olefin and functionalized olefin monomers. Each of the above elements of the present invention is fully described herein below.

DETAILED DESCRIPTION

The present invention provides a process for polymerizing olefin monomers, in particular ethylene, in the presence of catalysts taken from the selected family of salicylaldimine late transition metal chelates and to catalyst compositions composed of said salicylaldimine chelates in combination with an adjunct agent and/or a Lewis base, to produce polyolefins which can be substantially linear and have a weight average molecular weight of at least 1000.

It has been presently found that certain salicylaldimine late transition metal chelates can provide catalyst systems for the homopolymerization of ethylene and copolymerization of ethylene and functionalized olefins to provide high molecular weight, substantially linear polymer products. The catalyst of the present invention can be represented by the following general formula:

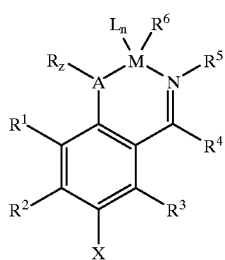

(I)

wherein

R represents a $C_1$–$C_{11}$ alkyl, aryl, or substituted aryl provided z is 1 when A is nitrogen and z is 0 when A is oxygen or sulfur;

$R^1$ represents a hydrogen atom, $C_1$–$C_{11}$ alkyl (preferably $C_1$–$C_5$ and most preferably tert-butyl); aryl, such as phenyl, biphenyl, terphenyl, naphthyl, anthracyl, phenanthracyl and the like; substituted aryl wherein the substitution group is selected from $C_1$–$C_6$ alkyl, perfluoroalkyl, nitro, sulfonate, or halo group; arylalkyl, such as toluyl and the like; halo, such as chloro, bromo, and the like; nitro group; sulfonate group; siloxyl $OSiE_3$ where E is selected from phenyl or $C_3$–$C_4$ alkyl such as isopropyl or butyl and the like); or a hydrocarbyl terminated oxyhydrocarbylene group, —(BO)$_z$$R^7$, wherein each B independently represents a $C_1$–$C_4$ (preferably $C_2$–$C_3$) alkylene group or an arylene group (preferably phenyl and especially the B group adjacent to the basic structure to which the $R^1$ is bonded); $R^7$ represents a $C_1$–$C_{11}$ (preferably a $C_1$–$C_3$) hydrocarbyl group such as an alkyl or an unsubstituted or substituted aryl group, such as phenyl, biphenyl, naphthyl and the like, alone or substituted with one or more $C_1$–$C_6$ alkyl, and z is 1 to 4. $R^1$ is preferably a steric bulky group selected from aryl, substituted aryl or a branched $C_3$–$C_6$ alkyl group or an alkoxyalkyl group and, most preferably, phenyl, anthracyl, phenanthracyl, terphenyl or t-butyl:

$R^2$ represents hydrogen atom, aryl, substituted aryl, $C_1$–$C_{11}$ alkyl, halogen atom or $R^1$ and $R^2$ can, together, provide a hydrocarbylene or substituted hydrocarbylene which forms a carbocyclic ring which may be non-aromatic or aromatic; $R^2$ is preferably hydrogen or, taken with $R^1$ as a carbocyclic ring group:

$R^3$ represents hydrogen:

$R^4$ represents hydrogen atom, a $C_1$–$C_{11}$ alkyl, an aryl group such as a phenyl or a substituted aryl group such as 2,6-dimethylphenyl and the like, and is preferably selected from hydrogen, $R^5$ represents a $C_1$–$C_{11}$ alkyl group (preferably a $C_4$–$C_8$ alkyl group) such as methyl, ethyl, propyl, t-butyl, and the like, a cycloalkyl group such as cyclohexyl and the like, an aryl group, such as phenyl, biphenyl, naphthyl and the like, or a substituted aryl having one or both ortho positions of the aromatic group (especially the phenyl group) substituted with a $C_1$–$C_4$ alkyl and/or the para position (with respect to the N—$R^5$ bond) substituted with a hydrogen atom, nitro, trifluoromethyl, halogen atom, methoxy, or $C_1$–$C_4$ alkyl or fused or unfused aryl, sulfonate, or a hydrocarbyl terminated oxyhydrocarbylene group —(BO)$_z$$R^7$ as defined in $R^1$ above. $R^5$ is preferably a t-butyl or a cycloalkyl such as adamantyl, or a 2,6-di($C_1$–$C_4$ alkyl)phenyl group and most preferably 2,6-diisopropylphenyl or 2,6-diisopropyl-4-nitrophenyl:

$R^1$ and $R^5$ can, together, form an oxyhydrocarbylene chain, e.g., —(BO)$_m$B— wherein each B independently represents a $C_1$–$C_4$ alkylene group or an arylene group and m is an integer of from 2 to 5 preferably 3–5;

n is an integer of 0 or 1;

$R^6$ represents, when n is 1, an unsubstituted or substituted aromatic group, such as phenyl which is preferably unsubstituted, a $C_1$–$C_{11}$ alkyl (preferably a $C_1$–$C_5$ alkyl and most preferably methyl), a hydrogen atom or halogen atom (preferably chloro or bromo), or when n is 0, $R^6$ repesents an allyl or substituted allyl group wherein the substitution can be selected from a halogen atom, a nitro group or a sulfonate group:

L represents a coordination ligand such as triphenylphosphine, tri($C_1$–$C_6$ alkyl) phosphine, tricycloalkyl phosphine, diphenyl alkyl phosphine, dialkyl phenylphosphine, trialkylamine, arylamine such as pyridine, $C_2$–$C_{20}$ alkene such as octene, decene, dodecene, allyl and the like, a substituted alkene wherein the substitution group may be selected from a halogen atom (preferably chloro), an ester group, a $C_1$–$C_4$ alkoxy group, an amine group (—$NR_2$ wherein each R is hydrogen, or a $C_1$–$C_3$ alkyl), carboxylic acid or its alkali metal salt, di($C_1$–$C_3$)alkyl ether, tetrahydrofuran, a nitrile such as acetonitrile and the like:

X represents any electron withdrawing group such as $NO_2$, halo (chloro, bromo and the like), persulfonate ($SO_3^-$), sulfonyl ester ($SO_2R$), carboxyl ($COO^-$), a perfluoroalkyl or a hydrogen atom. The sulfonate or carboxylate is associated with an alkali or alkaline earth metal cation. Less preferably, X may represent an electron donating group such as alkoxy:

M represents one of the transition metals, that is a Group IV or VIII transition metal selected from Fe, Co, Ni, Ru, Rh, Pd, Os, Ir, Pt in the +2 oxidation state or Ti, Zr, Hf in the +4 oxidation state and preferably a late transition metal selected from iron, cobalt, nickel or palladium and most preferably either nickel or palladium:

A represents oxygen, sulfur or nitrogen.

The present invention provides a catalyst which contains sterically bulky groups both above and below as well as within the plane of orientation with respect to the transition metal of the complex. It is believed, though not meant to be a limitation of the invention, that the steric and electronic configuration of the presently achieved complex provides the following desired characteristics:

(1) it utilizes late transition metals (preferably Ni or Pd) to provide high resistance to deactivation by oxygenated species;

(2) it contains certain bidentate, chelating ligand groups which are believed to enhance the selectivity-controlling effect in the polymerization of ethylene and of α-olefins;

(3) it contains groups of extreme steric bulk which provide shielding or partial shielding of the axial faces of the transition metal square planar complexes and thereby it is believed, retards associative displacement and chain transfer during the polymerization;

(4) the steric bulk which is within the plane of the transition metal square planar complex may inhibit chain migration processes and thereby cause substantially linear polymerization; and (5) the steric bulk which is within the plane of the transition metal square planar complex may promote dissociation of the ancillary ligand, L, and thereby result in an increase in the number of active polymerization sites.

The catalysts (I) are most preferably those having bulky substituents, such as aryl as, for example, terphenyl, anthracenyl, phenanthracenyl and the like and substituted aryl groups such as 2,6-diisopropylphenyl, in the $R^1$ and/or $R^5$ positions and further may have an electron-withdrawing group in the X position or as a substituent of the $R^1$ and/or $R^5$ group, preferably when such groups are aryl or substituted aryl type groups.

The catalyst (I) of the present invention may further contain an ether or polyether group as part of structure of the subject salicylaldimine ligand. The incorporation of such group(s) can be made at $R^1$ and/or at $R^5$ or as an oxyhydrocarbylene chain between $R^1$ and $R^5$ such that a hydrocarbon moiety of said oxyhydrocarbylene is directly bonded to the nitrogen atom at $R^5$ and to the aromatic ring at $R^1$. Such catalysts provide enhanced catalytic activity over catalyst (I) absent said group(s) and do not need the use of adjunct agent or Lewis base additive, as described herein below.

Synthesis of the precursor ligands can be achieved by reacting the appropriate salicylaldehyde (having desired substituent groups on the phenyl ring) with a primary amine ($R^5NH_2$), such as 2,6-diisopropylaniline or 2,6-diisopropyl-4-nitroaniline and the like. The reaction can be carried out in solution, such as a $C_1$–$C_5$ alcohol (e.g. methanol, ethanol or the like) or aromatic compound (e.g., benzene, toluene or the like). The reaction is preferably carried out at temperatures of from about 15° C. to 80° C. (most preferably at from 15 to 25° C.) for a period of from one to twenty hours (most preferably from 10 to 12 hours). The reaction is carried out at atmospheric pressure and in the presence of a catalytic amount of an organic acid, such as formic acid or acetic acid to provide the salicylaldimine ligand (IV) according to the equation below:

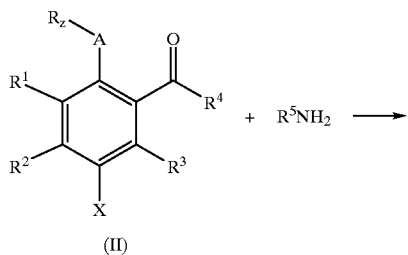

(II)

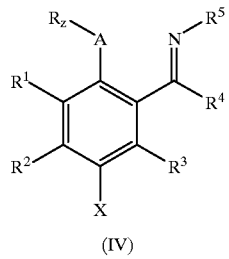

(IV)

The bidentate ligand (IV) can be deprotonated using a lithium alkyl or an alkali metal hydride (e.g., NaH being preferred), as illustrated herein below to form the alkali metal salt (V). The deprotonation is carried out at low temperatures such as about 0° to 30° C. (preferably 0° to 10° C.) at normal atmospheric pressure and in the presence of an inert solvent, such as tetrahydrofuran, dialkyl ether, $C_5$–$C_{10}$ hydrocarbon, dioxane and the like. The reaction normally is completed in a short period, such as from about 5 to 30 minutes. The alkali metal salt (V) can then be reacted with a late transition metal coordination compound of the type $R^6(L)_2MY$, wherein each $R^6$ and L are as defined above, and Y represents a halogen atom, as for example bis (triphenylphosphine)phenyl nickel chloride, and the like. This reaction may be conducted in an inert solvent, such as tetrahydrofuran, dialkyl ether, $C_5$–$C_{10}$ hydrocarbon, and the like at temperatures of from about 10 to 90° C. (preferably 10° to 30° C.) for periods of from one to fifteen hours (normally 10–15 hours) to provide catalyst (I) as follows:

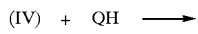

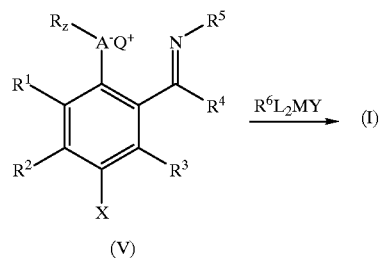

(V)

R in formulas II and IV each independently represents hydrogen atom, a $C_1$–$C_{11}$ alkyl, aryl, or substituted aryl provided that R represents at least one hydrogen atom and z is 1 when A is oxygen or sulfur and z is 2 when A is nitrogen. R and z in formula V represents those groups as defined with respect to formula I above. Each of the remaining symbols $R^1$, $R^2$, $R^3$, $R^4$, $R^5$, $R^6$, M, Y, L and X represent the groups defined above with respect to catalyst I.

In the above, the $R^1$ may be hydrogen but preferably is a bulky group which provides a steric shield of the transition metal's equatorial face by being well-positioned in the plane of the transition metal complex as well as some bulk in the axial face. For example, $R^1$ is preferably an aryl, such as phenyl, biphenyl, terphenyl, naphthyl, anthracenyl or phenanthracenyl, or nitro-substituted aryl, or a bulky alkyl, such as a tert-butyl group. Such substituted salicylaldehydes (II) are readily formed by formylation of an appropriately substituted phenol. This is conventionally accomplished by reacting the substituted phenol with an aldehyde source, such as formaldehyde (e.g., paraformaldehyde, 1,3,5-trioxane) or dimethylformamide in the presence of stannous chloride catalyst according to the procedures described by Casirighi et al in J. Chem. Soc. Perkins Trans. I, 1980, 1862–5, the teachings of which are incorporated herein by reference in its entirety.

As indicated above, $R^1$ may be selected from sterically bulky groups other than hydrocarbyl groups as, for example, siloxane groups. Such substitution can be readily accomplished by using 2,3-dihydroxybenzaldehyde as the starting material II to form the Schiff base aldimine compound IV. The 3-position hydroxyl group can then be converted to a siloxy group by reaction with the appropriate aryl, alkyl or mixed substituted silyl halide as, for example triisopropyl silyl chloride, diphenyl-t-butyl silyl chloride, triphenyl silyl chloride and the like. Deprotonation and reaction with transition metal coordination compound of the type $R^6(L)_2MY$ provides the desired catalyst compound I in the manner described above.

As defined above, $R^1$ and $R^5$ may each independently be selected from a hydrocarbyl terminated oxyhydrocarbylene containing group. Such groups may be represented as —$(BO)_zR^7$ wherein each B independently represents a $C_1$–$C_4$ (preferably a $C_2$–$C_3$) alkylene group or an arylene group and $R^7$ represents a $C_1$–$C_{11}$ (preferably $C_1$–$C_3$) hydrocarbyl group such as alkyl, an aryl, an alkaryl, or an aralkyl group and z represents an integer of 1 to 4. Such oxyhydrocarbylene group may be made part of compound I by mono-alkylation of 2,2'-dihydroxybiphenyl at one OH group with bromoethyl ether, followed by formylation (with an aldehyde source) of the other phenolic ring adjacent to the OH, followed by imine formation and finally metallation with $R^6(L)_2MY$ in the manner described previously.

Further, it has been found that desired catalyst can be in the form of compound (I) when the aryl group is substituted with an electron withdrawing group X, as defined above. For example, the salicylaldehyde may be substituted with a nitro, halo, trifluoromethyl, sulfonate, sulfonyl or carboxyl group in the 5-position. Some of the substituted salicylaldehydes are commercially available. They may be further reacted with the substituted aniline or aniline derivative as described above to provide the bidentate ligand IV. The ligand is then formed into the transition metal complex I, in the manner described above.

It has been found that substituted salicylaldimine complexes of late transition metals described above provide catalytic activity for olefin (e.g., ethylene) polymerization and provide substantially linear product having a low degree of branching. These complexes are neutral compounds and, as such do not require the presence of organo aluminum or partially hydrolyzed organo aluminum compounds or other reducing agent to cause activation of the complex towards olefin insertion reaction and polymerization. However, organo aluminum and hydrolyzed organo aluminum compounds, such as methyl alumoxane or trialkyl aluminum compounds and the like, may be present and are preferably present when $R^6$ is halogen. Compounds I are a new family of complexes of single-site catalysts.

The subject catalysts may be used as the sole catalyst (this is especially acceptable when the bulky group $R^1$ is large such as phenyl, biphenyl, terphenyl, anthracenyl, phenanthracenyl, nitro-substituted aryl or the like) or may be used in combination with an adjunct agent and/or a Lewis base (preferred). The adjunct agent comprises known phosphine sponge material capable of facilitating phosphine (ligand L) dissociation and trapping of free phosphine. Such catalyst composition adjunct agents are, for example, bis(cyclooctadiene)-nickel, tris(pentafluorophenyl)boron, 9-borabicyclo[3.3.]nonane (9-BBN), methyl iodide, and the like.

It has unexpectedly been found that the subject catalyst provides an enhanced catalyst composition when combined with a Lewis base as, for example ethers, esters, aldehydes, ketones, alcohols, amides, organic carbonates, organonitro compounds, or mixtures thereof and even water. It is commonly believed that organometallic catalysts should be combined with Lewis acid compounds to provide effective catalyst systems and that water acts as a poison to such catalysts. In contrast to the present finding, it has been previously deemed important to use conventional single site catalysts, such as metallocene catalysts, in the absence of moisture or other oxygenated compounds in order to provide an effective catalyst system.

The Lewis base additives found useful in forming a catalyst composition with the catalyst of compound I or V comprise ether compounds, such as dialkyl ethers where each alkyl group is independently selected from a $C_1$–$C_{18}$ alkyl, preferably a $C_1$–$C_5$ alkyl group as, for example, diethyl ether, methyl ethyl ether, diisopropyl ether, ethyl propyl ether, dibutyl ether and the like; vinyl ethers as, for example, ethyl vinyl ether; aryl ethers as, for example, dibenzyl ether, diphenyl ether, dinaphthyl ether and the like, mixed ethers as, for example, amyl phenyl ether, methyl benzohydryl ether, benzyl phenyl ether, anisole, phenetole and the like. The ether additive may also be selected from cyclic ethers as, for example, tetrahydrofuran, dioxane-1,4, dioxane-1,3, crown ethers such as 18-crown-6, 14-crown-5, 12-crown-4 and the like as well as polyethers such as dimethoxyethane, diglyme, triglyme, pentaglyme, or polyoxyalkylenes as, for example, polyoxyethylene (preferably lower molecular weight polymers which are miscible in the polymerization solvent used).

The above ethers, especially the alkyl and/or aryl group containing ethers and cyclic ethers described above, and most preferably dialkyl ether (diethyl ether) and low molecular weight polyethers (dimethoxy ethane), have been found to be effective solvents or co-solvents for use in the polymerization process when the subject catalyst of compound I or compound V is used, as described herein below.

The Lewis base may be selected from an organic ester represented by the formula

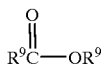

wherein each $R^9$ is independently selected from a $C_1$–$C_{11}$ alkyl group, preferably a $C_1$–$C_5$ alkyl group as, for example, ethyl acetate, propyl acetate, hexyl acetate, ethyl butyrate, propyl butyrate, ethyl caproate, ethyl caprylate, ethyl laurate and the like.

Further, aldehydes and ketones have been found useful as a Lewis base additive in forming the subject catalyst composition. They may be represented by the formula

wherein $R^{10}$ represents a $C_1$–$C_{12}$ hydrocarbyl selected from unsubstituted or substituted (e.g., carbonyl) alkyl, aryl, alkaryl or aralkyl groups and $R^{11}$ represents a hydrogen atom or an $R^{10}$ group, which is independently selected. For example, the aldehyde or ketone may be selected from acetone, propanone, butyrone, 4-heptanone, 2,4-pentanedione and the like, as well as cyclic ketones such as cyclohexanone, 1,4-cyclohexanedione and the like, or an aldehyde such as acetaldehyde, capraldehyde, valeraldehyde and the like.

Still further, an alcohol can be used as the Lewis base additive in forming the subject catalyst composition. They may be selected from monohydric or polyhydric alcohols including, for example, alcohols having hydrocarbyl moiety composed of a $C_1$–$C_{12}$ (preferably $C_1$–$C_3$) alkyl, aryl (e.g., phenyl or benzyl), alkaryl and aralkyl groups. Examples of such alcohols include methanol, ethanol, propanol, isopropanol, butanol, t-butanol, 2-pentanol, 3-hexanol, glycol, 1,2,3-propanetriol, phenol, phenethyl alcohol, para-methyl phenol and the like.

Amides can be used as the Lewis base additive in forming the subject catalyst composition. The amides may be represented by the formula

wherein $R^{12}$ and $R^{13}$ each independently represent a $C_1$–$C_{11}$ hydrocarbyl, $R^{14}$ represents hydrogen or a $C_1$–$C_{11}$ hydrocarbyl. $R^{13}$ and $R^{14}$ are, preferably, independently selected from a $C_1$–$C_3$ alkyl group.

Nitroalkanes and nitroaromatics have also been found to be useful as a Lewis base additive in forming the subject catalyst composition. The nitroalkanes may be a mono (preferred) or poly nitro compound formed with a $C_1$–$C_{11}$ (preferably a $C_1$–$C_3$) alkyl group. The aromatic nitro should be a mono nitro compound such as nitrobenzene and the like.

It has been unexpectedly found that the subject catalyst composition may contain small amounts of water and that the presence of water does not destroy the activity of the catalyst of the subject invention. Thus, unlike most organometallic catalysts useful in olefin polymerization, the presently described catalyst can be used in the presence of small amounts of moisture to provide a catalyst composition which can remain active in the polymerization of olefins or mixtures of olefins and functional olefin monomer(s).

The amount of the Lewis base (except water) additive can be substantially any amount desired with from $10^0$ to $10^4$ times the amount of compound I or V on a molar basis being preferred and most preferred, from $10^1$ to $10^3$ times the molar amount of catalyst when ether or low molecular weight polyether is the Lewis base used and from $10^0$ to $10^2$ the molar amount of catalyst when other Lewis bases are used. In the case of water, the molar ratio of water to compound I or V which may be present can range from 0 to about $10^2$, preferably from 0 to $10^1$.

This invention concerns processes for making polymers, comprising, contacting the subject catalyst composition with one or more selected olefins or cycloolefins, alone or optionally with a functional α-olefin such as a carboxylic acid of the formula $CH_2=CH(CH_2)_mCOOH$, a carboxylic acid ester of the formula $CH_2=CH(CH_2)_mCO_2R^{15}$ or $CH_2=CHOCOR^{15}$, an alkyl vinyl ether of the formula $CH_2=CH(CH_2)_mOR^{15}$, vinyl ketones of the formula $CH_2=CH(CH_2)_mC(O)R^{15}$, a vinyl alcohol of the formula $CH_2=CH(CH_2)_mOH$, or a vinyl amine of the formula $CH_2=CH(CH_2)_mNR^{16}$, wherein m is an integer of 0 to 10 and $R^{15}$ is a $C_1$–$C_{10}$ hydrocarbyl group, aryl or substituted aryl group (preferably methyl) and $R^{16}$ is independently selected from hydrogen or an $R^7$ group; a functional cycloolefin, such as functionalized norbornene wherein the functional group is an ester, alcohol, carboxylic acid, halogen atom, a primary, secondary or tertiary amine group or the like; or unsaturated dicarboxylic acid anhydride or carbon monoxide or the like and other selected monomers such as vinyl halides. The "polymerization process" described herein (and the polymers made therein) is defined as a process which produces a polymer with a molecular weight (Mw) of at least about 1000.

The subject catalysts may generally be written as

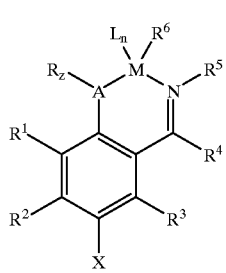

(I)

wherein each symbol R, $R^1$, $R^2$, $R^3$, $R^4$, $R^5$, $R^6$, L, M, A and X are defined above. Preferably M is Ni(II) or Pd(II).

Alternately, the catalytic polymerization of the present invention can be carried out by contacting one or more selected olefins or cycloolefins alone or optionally with a functional olefin monomer, as described above with a catalyst composition formed in-situ and composed of one or more bidentate ligand (V) described above in combination with a transition metal (M) organic complex, $R^6(L)_2MY$. The ligand (V) and complex should be used in about a 1:1 molar ratio. In a preferred embodiment of the present invention, the bidentate ligand V is combined with a transition metal organic complex of the formula $R^6(L)_2MY$ in about a 1:1 molar ratio in the presence of olefin and/or cycloolefin alone or optionally with a functional olefin monomer. The catalyst composition composed of ligand (V) and transition metal organic complex may further contain a phosphine sponge and/or a Lewis base additive, such as those described above, or an organo aluminum or hydrolyzed organo aluminum compound or mixtures thereof as described above with respect to catalyst compositions composed of compound (I) which have a halogen as $R^6$.

In all catalysts and precursor bidentate ligands, described herein, it is preferred that $R^1$ and $R^5$ are each independently a sterically bulky hydrocarbyl. In one form it is especially preferred that $R^1$ and $R^5$ are each independently aryl or substituted aryl groups. In another form, it is preferred that $R^1$ and/or $R^5$ be independently selected from a hydrocarbyl terminated oxyhydrocarbylene containing group, as described above. It is also preferred that $R^1$ and $R^2$ are each taken together to provide a hydrocarbylene which forms a carbocyclic ring. It is further preferred that X, when present, be an electron-withdrawing group such as nitro, trifluoromethyl, sulfonate, sulfonyl or carboxylate and the likes thereof. It is preferred that when $R^5$ is a substituted aryl, the 4 position of the aryl (with respect to the N— bond) be either hydrogen or nitro.

When using I or V as a catalyst in the manner described above, it is preferred that $R^2$, $R^3$ and $R^4$ are hydrogen or methyl, unless $R^2$ is, when taken together with $R^1$, a $C_4$–$C_{10}$ carbocyclic group which may or may not be aromatic. It is also preferred that either or both $R^1$ and $R^5$ are biphenyl, terphenyl, anthracenyl, phenanthracenyl, 2,6-diisopropylphenyl, 2,6-dimethylphenyl, 2,6-diethylphenyl, 4-methylphenyl, 2-isopropyl-6-methylphenyl, phenyl, 2,4,6-trimethylphenyl, 2-t-butylphenyl, 2-t-butyl-4-methylphenyl, 2,6-diisopropyl-4-nitrophenyl, and 10-nitroanthracenyl.

The structure of the ligand associated with compound I or compound V may influence the polymer microstructure and polymer molecular weight. For example, it is preferred that $R^1$ be a bulky aryl or substituted aryl group. Complexes with $R^1$ of this type generally produce higher molecular weight and more linear polymer product for any given set of conditions. The catalyst or the catalyst composition of I or V with the phosphine sponge adjunct and/or organo aluminum compound adjunct, or with the Lewis base additive or mixtures of adjunct and Lewis base when optionally used, are contacted, usually in the liquid phase, with ethylene or other olefin ($RCH=CH_2$), and/or 4-vinylcyclohexane, 4-vinylcyclohexene, cyclopentene, cyclobutene, substituted norbornene, or norbornene. The liquid phase may include a compound added just as a solvent and/or may include the monomer(s) itself and/or may comprise the Lewis base (especially an ether compound) in the liquid phase at reaction conditions. When an adjunct is used, the molar ratio of adjunct to compound I or V is from about 0.001:1 to 15:1, preferably about 0.01:1 to about 8:1, and most preferably from 0.1:1 to 3:1. The temperature at which the polymerization is carried out is from about −100° C. to about +200° C., preferably about −20° C. to about +100° C. and most preferably between about 0° C. and 90° C. All ranges of temperatures being covered by this teaching. The pressure at which the polymerization is carried out is not critical, atmospheric pressure to about 100 MPa, or more, being a suitable range. The pressure may affect the yield, molecular weight and linearity of the polyolefin produced, with increased pressure providing more linear and higher molecular weight polymer product.

Preferred alpha-olefins and cyclic olefins in the polymerization are one or more of ethylene, propylene, 1-butene, 2-butene, 1-hexene, 1-octene, 1-pentene, 1-tetradecene, norbornene, and cyclopentene, with ethylene, propylene, cyclopentene and norbornene being more preferred. Ethylene (alone as a monomer) is especially preferred.

The polymerization may be run in the presence of various liquids. The solvent in which the polymerization may be conducted can be selected from (i) the monomer(s), per se or (ii) any organic compound which is liquid under the reaction conditions and is substantially inert to the reactants and product, or (iii) a Lewis base additive (except water which, when used, should be present in limited amounts) which is liquid under the reaction conditions, or mixtures thereof. Particularly preferred are aprotic organic liquids or organic ethers or mixtures thereof. The catalyst system, monomer(s), and polymer may be soluble or insoluble in these liquids, but obviously these liquids should not prevent the polymerization from occurring. Suitable liquids include alkanes, cycloalkanes, halogenated hydrocarbons, ethers, and aromatic and halogenated aromatic hydrocarbons. Specific useful solvents include hexane, heptane, toluene, xylenes, and benzene, methylene chloride, ethyl ether, dimethoxyethane, tetrahydrofuran and crown ethers.

The catalyst compositions of the present invention cause polymerization of one or more alpha-olefin, with functional olefins such as those described herein above. When carbon monoxide is used as a comonomer, it forms alternating copolymers with the various alpha-olefins. The polymerization to form the alternating copolymers is carried out with both CO and the olefin simultaneously present in the process mixture, and in the presence of the present catalyst composition.

The catalyst of the present invention may also be supported on a porous solid material (as opposed to just being added as a suspended solid or in solution), for instance on silica gel, zeolite, crosslinked organic polymers such as styrene-divinylbenzene copolymer and the like. By supported is meant that the catalyst may simply be carried physically on the surface of the porous solid support, may be adsorbed, or may be carried by the support by other means.

In many of the polymerizations, certain general trends may occur, although for all of these trends there are exceptions. Pressure of the monomers (especially gaseous monomers such as ethylene) has an effect on the polymerizations in many instances. Higher pressure often reduces branching and extends polymer chain length, especially in ethylene containing polymers. Temperature also affects these polymerizations. Higher temperature usually increases branching.

In general, the period of time during which the catalysts of compound I or the catalyst composition having compound V remains active can be extended greatly based on a particular ligand structure, polymerization temperature, or type of Lewis present. Catalyst lifetime is long when Lewis base such as ether or dimethyoxyethane is present, co-catalyst adjunct is absent, and $R^1$ is a bulky aryl or substituted aryl group.

When the polymer product of the present invention is a copolymer of functionalized group containing monomer, the functional group may be further used to cross-link the polymer. For example, when copolymers of an olefinic carboxylic acid or olefinic ester and an alpha-olefin are made, they may be crosslinked by various methods known in the art, depending on the specific monomers used to make the polymer. For instance, carboxyl or ester containing polymers may be crosslinked by reaction with diamines or with diisocyanates to form bisamides. The carboxyl groups may also be neutralized with a monovalent or divalent metal containing base (e.g., NaOH, CaO) to form ionomeric or pseudo-crosslinked polyolefin copolymer.

The resultant polymers formed according to the present invention, especially those of ethylene homo or copolymers may have varying degrees of branching in the polymer. Branching may be determined by NMR spectroscopy (see the Examples for details), and this analysis can determine the total number of branches, the branching distribution and to some extent the length of the branches. Herein the amount of branching is expressed as the number of branches per 1000 of the total methylene ($—CH_2—$) groups in the polymers, with one exception. Methylene groups that are in an ester grouping, i.e., $—CO_2R$; a ketone group, i.e., $—C(O)R$ are not counted as part of the 1000 methylenes. For example, ethylene homopolymers have a branch content of about 0 to about 150 branches per 1000 methylene groups, preferably about 5 to about 100 and most preferably about 3 to about 70 branches per 1000 methylene groups. These branches do not include polymer end groups. Alternately, branch content can be estimated from correlation of total branches as determined by NMR with polymer melting point as determined by differential scanning calorimetry.

The polymers formed by the present invention may be mixed with various additives normally added to elastomers and thermoplastics [see EPSE (below), vol. 14, p. 327–410] which teaching is incorporated herein by reference. For instance reinforcing, non-reinforcing and conductive fillers, such as carbon black, glass fiber, minerals such as silica, clay, mica and talc, glass spheres, barium sulfate, zinc oxide, carbon fiber, and aramid fiber or fibrids, may be used. Antioxidants, antiozonants, pigments, dyes, slip agents, anti-fog agents, antiblock agents, delusterants, or compounds to promote crosslinking may be added. Plasticizers such as various hydrocarbon oils may also be used.

The polymers formed by the present invention may be used for one or more of the applications listed below. In some cases a reference is given which discusses such uses for polymers in general. All of these references are hereby included by reference. For the references, "U" refers to W. Gerhartz, et al., Ed., Ullmann's Encyclopedia of Industrial Chemistry, 5th Ed. VCH Verlagsgesellschaft mBH, Weinheim, for which the volume and page number are given, "ECT3" refers to the H. F. Mark, et al., Ed., Kirk-Othmer Encyclopedia of Chemical Technology, 4th Ed., John Wiley & Sons, New York, "ECT4" refers to the J. I. Kroschwitz, et al., Ed., Kirk-Othmer Encyclopedia of Chemical Technology, 4th Ed., John Wiley & Sons, New York, for which the volume and page number are given. "EPST" refers to H. F. Mark, et al., Ed., Encyclopedia of Polymer Science and Technology, 1st Ed., John Wiley & Sons, New York, for which the volume and page number are given, "EPSE" refers to H. F. Mark, et al., Ed., Encyclopedia of Polymer Science and Engineering, 2nd Ed., John Wiley & Sons, New York, for which volume and page numbers are given, and "PM" refers to J. A. Brydson, ed., Plastics Materials, 5th Ed., Butterworth-Heinemann, Oxford, UK, 1989, and the page is given. In these uses, a polyethylene, polypropylene and a copolymer of ethylene and propylene are preferred.

1. The polyolefins herein are especially useful in blown film applications because of their particular rheological properties (EPSE, vol. 7, p. 88–106). It is preferred that these polymers have some crystallinity.
2. The polymers are useful for blown or cast films or as sheet (see EPSE, vol. 7 p. 88–106; ECT4, vol. 11, p 843–856; PM, p. 252 and p. 432ff). The films may be single layer or multilayer, the multilayer films may include other polymers, adhesives, etc. For packaging the films may be stretch-wrap, shrink-wrap or cling wrap and may also be heat sealable. The films are useful for many applications such as packaging foods or liquids, geomembranes and pond liners. It is preferred that these polymers have some crystallinity.
3. Extruded films or coextruded films may be formed from these polymers, and these films may be treated, for example by uniaxial or biaxial orientation after crosslinking by actinic radiation, especially electron beam irradiation. Such extruded films are useful for packaging of various sorts. The extruded films may also be laminated to other films using procedures known to those skilled in the art. The laminated films are also useful for packaging of various sorts.
4. The polymers, particularly the elastomers, may be used as tougheners for other polyolefins such as polypropylene and polyethylene.
5. Tackifiers for low strength adhesives (U, vol. A1, p 235–236) are a use for these polymers. Elastomers and/or relatively low molecular weight polymers are preferred.
6. An oil additive for smoke suppression in single-stroke gasoline engines is another use. Elastomeric polymers are preferred.
7. The polymers are useful as base resins for hot melt adhesives (U, vol. A1, p 233–234), pressure sensitive adhesives (U, vol. A1, p 235–236) or solvent applied adhesives. Thermoplastics are preferred for hot melt adhesives.
8. Base polymer for caulking of various kinds is another use. An elastomer is preferred. Lower molecular weight polymers are often used.
9. Wire insulation and jacketing may be made from any of the polyolefins (see EPSE, vol. 17, p. 828–842). In the case of elastomers it may be preferable to crosslink the polymer after the insulation or jacketing is formed, for example by free radicals.

The following examples are provided herein below for illustrative purposes only and are not meant to be a limitation on the scope of the invention. All parts and percentages are by weight unless otherwise indicated.

EXAMPLE I

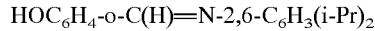

$HOC_6H_4\text{-}o\text{-}C(H)\!=\!N\text{-}2,6\text{-}C_6H_3(i\text{-}Pr)_2$

To a methanol (25 mL) solution of salicylaldehyde (10 g, 82 mmol) was added formic acid (1 mL) and 2,6-diisopropylaniline (21 g, 120 mmol). The resulting mixture was stirred for 1 hour. After this time, a yellow solid precipitated out of solution. The solid was collected by filtration through a glass frit and washed with methanol (2×10 mL) to yield 21 g (90%) of a yellow solid. $^1$H NMR($C_6D_6$): δ1.24 (d, 12H, $J_{HH}$=6.94 Hz), 3.07 (septet, 2H, $J_{HH}$=6.94 Hz), 7.02–7.48 (m, 7H), 8.39 (s, 1H), 13.12 (S, 1H); $^{13}$C NMR ($C_6D_6$): δ23.5, 28.2, 117.2, 119.1, 123.3, 125.6, 132.5, 133.3, 138.8, 146.4, 161.3, 167.0.

EXAMPLE II

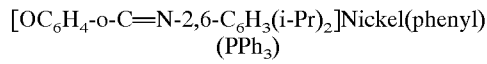

$[OC_6H_4\text{-}o\text{-}C\!=\!N\text{-}2,6\text{-}C_6H_3(i\text{-}Pr)_2]Nickel(phenyl)(PPh_3)$ In a Schlenk flask was dissolved the Na salt of the product of Example I (0.59 g, 1.5 mmol) and bis(triphenylphosphine)nickel(phenyl) chloride (1.0 g, 1.44 mmol) in benzene (20 mL). The reaction was stirred at room temperature for 1 hour. After this time, the reaction was filtered by cannula filtration, and the filtrate was concentrated in vacuo to ~5 mL. Pentane (30 mL) was added to the reaction. A yellow-orange solid precipitated from solution, and was isolated by cannula filtration to yield 0.74.g (76%) of a yellow-orange solid. $^1$H NMR ($C_6D_6$): δ1.03 (d, 6H, $J_{HH}$=6.84 Hz), 1.29 (d, 6H, $J_{HH}$=6.84 Hz), 4.05 (septet, 2H, $J_{HH}$=6.84 Hz), 6.31–7.69 (m, 27H), 7.93 (d, 1H, $J_{HP}$=8.80 Hz); $^{13}$C NMR ($C_6D_6$): δ22.6, 25.5, 28.8, 117.4, 120.0, 122.8, 125.3, 126.2, 128.3, 128.6, 129.7, 130.5, 131.0, 131.5, 133.3, 133.8, 134.0, 134.4 (d, $J_{CP}$=9.77 Hz), 137.4, 140.1, 149.4, 159.6, 165.2; $^{31}$P NMR ($C_6D_6$): δ25.94. Anal. Calcd for $C_{43}H_{42}NNiOP$: C, 76.35; H, 6.25; N, 2.07. Found: C, 76.20; H, 6.64; N, 1.89.

EXAMPLE III

$HO\text{-}(3\text{-}t\text{-}Bu)C_6H_3\text{-}o\text{-}C(H)\!=\!N\text{-}2,6\text{-}C_6H_3(i\text{-}Pr)_2$ To a methanol (25 mL) solution of t-butylsalicylaldehyde (10 g, 82 mmol) was added formic acid (1 mL) and 2,6-diisopropylaniline (21 g, 120 mmol). The resulting mixture was refluxed for 10 hours. After this time, the methanol was removed by rotary evaporation to yield a dark-brown oil. The oil was loaded onto a silica gel column and eluted with 90:10 hexane:ethyl acetate to yield 24 g (90%) of a viscous, orange oil. $^1$H NMR ($C_6D_6$): δ1.24 (d, 12H, $J_{HH}$=6.85 Hz), 1.56 (s, 9H), 3.10 (septet, 2H,$J_{HH}$=6.85 Hz), 6.94–7.49 (m, 6H), 8.39 (s, 1H), 13.71 (s, 1H); $^{13}$C NMR ($C_6D_6$): δ23.5, 28.2, 34.9, 118.3, 118.6, 123.3, 125.4, 130.5, 130.8, 137.6, 139.0, 146.4, 160.7, 167.6.

EXAMPLE IV

$HO\text{-}(3\text{-}Ph)C_6H_3\text{-}o\text{-}C(H)\!=\!N\text{-}2,6\text{-}C_6H_3(i\text{-}Pr)_2$ To a methanol (15 mL) solution of 6-phenyl salicylaldehyde (2.4 g, 12 mmol) was added formic acid (0.50 mL) and 2,6-diisopropylaniline (2.8 g, 16 mmol). The resulting mixture was refluxed for 10 hours. After this time, the methanol was cooled to room temperature at which time yellow crystals precipitated from the solution. The crystals was collected by filtration and washed with methanol (2×10 mL) to yield 3.0 g (70%) of a yellow solid. $^1$H NMR (C$_6$D$_6$): δ1.01 (d, 12H, J$_{HH}$=6.88 Hz), 2.96 (septet, 2H, J$_{HH}$=6.88 Hz), 7.05–7.74 (m, 11H), 7.92 (s, 1H), 13.90 (s, 1H); $^{13}$C NMR (C$_6$D$_6$): δ23.5, 28.5, 119.2, 119.3, 123.5, 125.9, 127.4, 127.7., 129.9, 130.8, 131.9, 134.7, 138.0, 138.9, 146.8, 159.4, 167.6.

EXAMPLE V

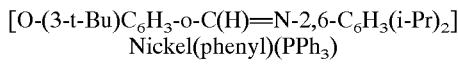
[O-(3-t-Bu)C$_6$H$_3$-o-C(H)=N-2,6-C$_6$H$_3$(i-Pr)$_2$] Nickel(phenyl)(PPh$_3$)

In a Schlenk flask was dissolved the Na salt of the product of Example III (2.1 g, 4.8 mmol) and bis(triphenylphosphine)nickel(phenyl)chloride (3.1 g, 4.4 mmol) in THF (50 mL). The reaction was stirred at room temperature for 1.5 hours. After this time, the reaction was filtered by cannula filtration and the filtrate was concentrated in vacuo to ~5 mL. Pentane (30 mL) was added with vigorous stirring and the reaction was cooled at −78° C. A yellow-orange solid precipitated from solution, and was isolated by cannula filtration to yield 3.5 g (83%) of a yellow-orange solid. $^1$H MNR (C$_6$D$_6$): δ0.93 (s, 9H), 1.08 (d, 6H, J$_{HH}$=5.88 Hz), 1.22 (d, 6H,J$_{HH}$=5.88 Hz), 4.28 (septet, 2H, J$_{HH}$=5.88 Hz), 6.21–7.83 (m, 26H), 7.97 (d, 1H, J$_{HP}$=9.12 Hz); $^{13}$C (C$_6$D$_6$): δ22.7, 25.5, 28.9, 29.8, 34.6, 113.9, 120.2, 121.0, 122.8, 125.0, 125.9, 128.3, 128.5, 129.1, 129.7, 131.5, 131.8, 132.2, 133.3, 134.9 (d,J$_{CP}$=10.4 Hz), 137.0, 140.8, 141.9, 150.2, 166.1, 166.8; $^{31}$P NMR (C$_6$D$_6$): δ23.35. Anal. Calcd for C$_{47}$H$_{50}$NNiOP: C, 77.06; H, 6.88; N, 1.91. Found: C, 76.93; H, 6.81; N, 1.63.

EXAMPLE VI

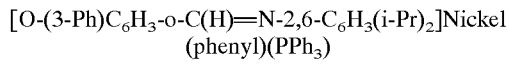
[O-(3-Ph)C$_6$H$_3$-o-C(H)=N-2,6-C$_6$H$_3$(i-Pr)$_2$]Nickel (phenyl)(PPh$_3$)

In a Schlenk flask was dissolved the Na salt of the product of Example IV (0.56 g, 1.6 mmol) and bis(triphenylphosphine)nickel(phenyl)chloride (1.0 g, 1.4 mmol) in benzene (20 mL). The reaction was stirred at reflux for 1 hour. After this time, the reaction was filtered by cannula filtration and the filtrate was concentrated in vacuo to ~5 mL. Pentane (30 mL) was added to the vigorously stirred solution. A light-green solid precipitated from solution, and was isolated by cannula filtration to yield 0.84 g (89%) of a yellow-orange solid. $^1$H NMR (C$_6$D$_6$): δ1.12 (d, 6H, J$_{HH}$=6.56 Hz), 1.21 (d, 6H, J$_{HH}$=6.56 Hz), 3.3 (s, 3H), 4.11 (septet, 2H, J$_{HH}$=6.56 Hz), 3.29 (s, 3H), 6.18–7.80 (m, 31H), 7.99 (d, 1H, J$_{HP}$=9.52 Hz); $^{13}$C NMR (C$_6$D$_6$): δ22.6, 25.6, 28.9, 114.4, 119.8, 121.1, 122.7, 125.0, 126.0, 127.4, 128.6, 129.4, 129.6, 131.7, 132.1, 134.0, 134.3, 134.4 (d,J$_{CP}$=9.76 Hz), 135.3, 136.8, 137.8, 140.1, 140.7, 150.0, 163.7, 166.5; $^{31}$P NMR (C$_6$D$_6$): δ21.87. Anal. Calcd for C$_{49}$H$_{46}$NNiOP: C, 78.20; H, 6.16; N, 1.86. Found: C, 77.69; H, 6.36; N, 1.42.

EXAMPLE VII 2-(9-Phenantrene)phenol-tetrahydropyran adduct

A solution of tetrahydropyran-protected phenol (10 g, 56 mmol) in diethyl ether (100 mL) was treated at room temperature with BuLi (44 mL, 70 mmol) for 4.5 hours. A solution of MgBr$_2$ was separately prepared by slowly adding 1,2-dibromoethane (5.3 mL, 62 mmol) to Mg turnings (1.6 g, 67 mmol) in diethyl ether (100 mL), and stirred for 4 hours. The Li-salt was added via cannula to the MgBr$_2$ solution to form the Grignard reagent. This solution was added to a cooled solution (−78° C.) of 9-bromophenanthrene (9.7 g, 38 mmol) and NiCl$_2$ (diphenylphosphinoethylene) (0.62 g, 1.2 mmol). The mixture was slowly warmed to room temperature and heated at reflux overnight. After this time, the reaction mixture was poured through a short silica gel column with 1:1 dichloromethane:hexane. The solvent was removed under vacuum to leave an orange, viscous oil. The yield of crude product was 14 g (70%). $^1$H NMR (CDCl$_3$): δ1.02–1.48 (m, 6H), 3.75 (m, 2H), 5.42 (d, 1H, J$_{HH}$=8.40 Hz), 7.20–8.81 (m, 13H); $^{13}$C NMR (C$_6$D$_6$): δ17.7, 18.3, 25.2, 30.1, 61.6, 62.0, 96.3, 96.9, 115.1, 115.4, 121.8, 121.9, 122.7, 126.1, 126.2, 126.3, 126.5, 126.7, 128.7, 129.2, 129.3, 130.1, 130.2, 130.5, 130.6, 131.5, 131.6, 131.7, 131.9.

EXAMPLE VIII 2-(Phenanthrene)salicylaldehyde

To a solution of 2-(9-phenanthrene)phenol (6.8 g, 25 mmol) and 2,6-lutidine (4.6 g, 43 mmol) in toluene (50 mL) was slowly added SnCl$_4$ (0.75 mL, 6.4 mmol). The solution was stirred at room temperature for 20 minutes. Paraformaldehyde was added (4.3 g, 140 mmol) and the reaction was stirred at 110° C. for 12 hours. After cooling to room temperature, the reaction mixture was poured into water (30 mL), and adjusted to pH 1 with concentrated HCl. The mixture was extracted with diethyl ether (500 mL), and the organic layer was washed twice with sat. brine and dried over Na$_2$SO$_4$. The solvent was removed by rotary evaporation to leave a yellow oil. The oil was loaded onto a silica gel column and eluted with 9:1 hexane:ethyl acetate. The yield of product was 1.9 g (26%). $^1$H NMR (CDCl$_3$): δ7.21–8.78 (m, 12H), 10.02 (s, 1H), 11.32 (s, 1H); $^{13}$C NMR (C$_6$D$_6$): δ120.0, 120.6, 122.7, 123.0, 126.6, 126.9, 127.0, 128.5, 128.8, 130.5, 130.8, 131.5, 133.8, 139.1, 159.6, 196.9.

EXAMPLE IX

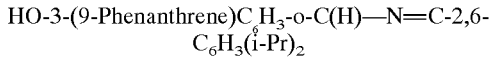
HO-3-(9-Phenanthrene)C$_6$H$_3$-o-C(H)=N=C-2,6-C$_6$H$_3$(i-Pr)$_2$ 2-(9-Phenanthrene)salicylaldehyde (1.9 g, 6.4 mmol), 2,6-diisopropylaniline (1.4 g, 7.9 mmol), and p-toluenesulfonic acid (65 mg, 0.34 mmol) was dissolved in benzene (27 mL). The solution was stirred at reflux overnight. After this time, the benzene was removed under vacuum. To the resulting oil was added hexane (100 mL) under vigorous stirring at which time a white solid precipitated. The solid was collected by filtration through a glass frit. A second crop of product was obtained from the filtrate to yield 1.7 g (58%). $^1$H NMR (CDCl$_3$): δ1.22 (d, 12H, J$_{HH}$=6.90 Hz), 3.07 (septet, 2H, J$_{HH}$=6.90 Hz), 7.14–8.90 (m, 15H), 8.46 (s, 1H), 13.45 (s, 1H); $^{13}$C NMR (C$_6$D$_6$): δ23.8, 28.2, 119.0, 122.7, 123.0, 123.4, 125.0, 126.6, 126.8, 127.2, 128.5, 128.9, 129.3, 130.4, 130.6, 131.2, 131.7, 132.2, 135.6, 138.9, 159.3, 166.9.

EXAMPLE X 2-(Anthracene)phenol-tetrahydropyran adduct

In a three-necked, 250 mL flask under an atmosphere of Ar was added Mg turnings (2.1 g, 87 mmol) in THF (20 mL). A few drops of 1,2-dibromoethane was added to activate the Mg. Then a solution of the tetrahydropyran-protected 2-bromophenol (22 g, 87 mmol) in THF (70 mL) was added dropwise, and the reaction was stirred at reflux overnight. After this time, the resulting slurry was added by cannula to a solution of 9-bromoanthracene (22 g., 88 mmol) and $NiCl_2(dppe)$ (1.4 g, 2.6 mmol) in THF (175 mL). The resulting solution was heated at reflux for 4 days. After this time, the solvent was removed in vacuo, and the oily residue was chromatographed on a silica gel column with 90:10 hexane:ethyl acetate. Removal of solvent yielded 10 g (34%) of a white crystalline solid. $^1H$ NMR ($CDCl_3$): δ0.87–1.30 (m, 6H), 3.42 (m, 1H), 3.60 (m, 1H), 5.30 (s, 1H), 7.25–8.49 (m, 13H); $^{13}C$ NMR ($C_6D_6$): δ17.7, 24.9, 30.0, 61.6, 61.9, 96.1, 96.4, 115.3, 115.8, 121.4, 121.7, 124.7, 125.2, 126.0, 126.6, 127.1, 127.5, 127.8, 128.2, 128.6, 129.0, 130.2, 130.3, 131.3, 132.5, 132.9, 133.9, 155.4.

EXAMPLE XI 2-(Anthracene)salicylaldehyde-tetrahydropyran adduct

To a diethyl ether (250 mL) solution of the tetrahydropyran-protected adduct of 2-(9-anthracene)phenol was added n-BuLi (28 mL, 43 mmol) dropwise. The resulting solution was stirred at room temperature for 4.5 hours. After this time, the solution was cooled to −78° C. and dimethyl formamide (5.4 mL, 70 mmol) was added to the reaction, which was allowed to warm to room temperature. After this time, the reaction was quenched with $H_2O$ and extracted with diethyl ether (200 mL). The organic layer was separated and dried with $Na_2SO_4$. The solvents were removed by rotary evaporation to yield a yellow solid. The solid was washed with hexane (50 mL) and dried in vacuo to yield 5.0 g (60%) product. $^1H$ NMR ($CDCl_3$): δ0.56–1.97 (m, 6H), 2.89 (m, 1H), 3.48 (m, 1H) 4.27 (m, 1H), 7.46–8.10 (m, 13H), 8.57 (s, 1H), 10.62 (s, 1H); $^{13}C$ NMR ($C_6D_6$): δ19.5, 24.6, 29.9, 64.2, 102.4, 124.6, 125.5, 126.1, 126.2, 126.5, 127.6, 128.0, 128.4, 128.7, 130.0, 130.4, 130.8, 131.2, 131.3, 131.9, 132.9, 159.0, 191.8.

EXAMPLE XII 2-(Anthracene)salicylaldehyde

The tetrahydropyran-protected 2-(9-anthracene) salicylaldehyde of Example XI (8.4 g, 22 mmol) was dissolved in ethanol (75 mL) and THF (100 mL). To the solution was added pyridinium p-toluenesulfonate (0.28 g, 1.1 mmol), and the reaction was stirred at reflux overnight. The solvents were removed in vacuo to yield 6.7 g (99%) of crude product. $^1H$ NMR ($CDCl_3$): δ7.25–8.55 (m, 13H), 10.05 (s, 1H), 11.22 (s, 1H); $^{13}C$ NMR ($C_6D_6$): δ120.0, 120.9, 125.3, 125.9, 126.1, 127.3, 127.6, 12.8.8, 130.3, 130.8, 131.5, 134.0, 140.4, 159.9, 196.9.

EXAMPLE XIII

HO-3-(9-Anthracene)$C_6H_3$-o-C(H)—N=C-2,6-$C_6H_3$(i-Pr)$_2$ 2-(Anthracene)salicylaldehyde (6.5 g, 22 mmol), 2,6-diisopropylaniline (4.6 g, 26 mmol), and p-toluenesulfonic acid (215 mg, 1.1 mmol) were dissolved in benzene (250 mL) and stirred under reflux for 3 hours in a Dean-Stark apparatus. After this time, the solvent was removed in vacuo, and the resulting residue was washed with hexane (100 mL) and methanol (20 mL), and dried in vacuo. The yield of product was 8.8 g (88%). $^1H$ NMR ($CDCl_3$): δ1.23 (d, 12H, $J_{HH}$=6.90 Hz), 3.09 (septet, 2H, $J_{HH}$=6.90 Hz), 7.23–8.52 (m, 15H), 8.59 (s, 1H), 13.33 (s, 1H); $^{13}C$ NMR ($C_6D_6$): δ23.8, 28.2, 119.0, 119.1, 123.4, 125.2, 125.6, 125.7, 126.7, 127.0, 127.3, 128.5, 128.8, 130.5, 131.6, 132.4, 132.5, 136.8, 138.9, 146.3, 159.6, 166.8.

EXAMPLE XIV

[O-3-(9-Phenanthrene)$C_6H_3$-o-C(H)—N=C-2,6-$C_6H_3$(i-Pr)$_2$]Nickel(phenyl)(PPh$_3$)

In a Schlenk flask was dissolved the Na salt of the product of Example IX (0.87 g, 1.6 mmol) and bis(triphenylphosphine)nickel(phenyl)chloride (1.0 g, 1.40 mmol) in benzene (20 mL). The reaction of was stirred at room temperature for 1.5 hours. After this time, the reaction was filtered by cannula filtration, and the filtrate was concentrated in vacuo to ~5 mL. Pentane (30 mL) was added with vigorous stirring. A yellow-orange solid precipitated from solution, and was isolated by cannula filtration to yield 0.92 g (75%) of a yellow-orange solid. $^1H$ NMR ($C_6D_6$): δ1.08 (d, 6H, $J_{HH}$=6.96 Hz), 1.19 (d, 6H, $J_{HH}$=6.96 Hz), 1.21 (d, 6H, $J_{HH}$=6.96 Hz), 1.32 (d, 6H, $J_{HH}$=6.96 Hz), 4.16 (septet, 2H, $J_{HH}$=6.96 Hz), 6.14–8.37 (m, 35H), 8.13 (d, 1H, $J_{HP}$=11.36 Hz); $^{13}C$ NMR ($C_6D_6$): δ22.6, 25.6, 28.9, 114.2, 119.9, 121.2, 122.8, 124.5, 124.7, 124.9, 125.6, 126.1, 127.2, 127.4, 128.4, 128.9, 130.5, 130.8, 131.1, 131.5, 131.8, 133.5 (d, $J_{CP}$=13.4 Hz), 134.7, 136.6, 137.4, 138.3, 140.7, 145.2, 146.4, 150.1, 165.2, 166.7; $^{31}P$ NMR ($C_6D_6$): δ25.09. Anal. Calcd for $C_{57}H_{50}NNiOP$: C, 80.29; H, 5.91; N, 1.64. Found: C, 80.06; H, 6.14; N, 1.25.

EXAMPLE XV

[O-3-(9-Anthracene)$C_6H_3$-o-C(H)—N=C-2,6-$C_6H_3$(i-Pr)$_2$]Nickel(phenyl)(PPh$_3$)

In a Schlenk flask was dissolved the Na salt of the product of Example XIII (0.53 g, 1.6 mmol) and bis(triphenylphosphine)nickel(phenyl)chloride (2.0 g, 2.9 mmol) in benzene (20 mL). The reaction was stirred at room temperature for 1.5 hours. After this time, the reaction was filtered by cannula filtration, and the filtrate was concentrated in vacuo to ~5 mL. Pentane (30 mL) was added with vigorous stirring and the reaction was cooled to −78° C. A yellow-orange solid precipitated from solution, and was isolated by cannula filtration to yield 0.71 mg (78%) of a yellow-orange solid. $^1H$ NMR ($C_6D_6$): δ1.14 (d, 6H, $J_{HH}$=6.56 Hz), 1.18 (d, 6H, $J_{HH}$=6.56 Hz), 4.16 (septet, 2H, $J_{HH}$=6.56 Hz), 6.17–7.83 (m, 40H), 8.15 (d, 1H, $J_{HP}$=11.32 Hz); $^{13}C$ NMR ($C_6D_6$): δ22.6, 25.6, 28.9, 114.2, 119.9, 121.2, 122.8, 124.5, 124.7, 124.9, 125.6, 126.1, 127.2, 127.4, 128.4, 128.9, 130.5, 130.8, 131.1, 131.5, 131.8, 133.5 (d, $J_{CP}$=13.4 Hz), 134.7, 136.6, 137.4, 138.3, 140.7, 145.2, 146.4, 150.1, 165.2, 166.7; $^{31}P$ NMR ($C_6D_6$): δ22.99. Anal. Calcd for $C_{57}H_{50}NNiOP$: C, 80.29; H, 5.91; N, 1.64. Found: C, 79.77; H, 6.09; N, 1.49.

EXAMPLE XVI 2,3-Dihydroxy,1-(2,6-diisopropyl)benzaldimine

In a round-bottom flask was dissolved 10 g (72 mmol) of 1,2-dihydroxybenzaldehyde, 2,6-diisopropylaniline (16 g, 90 mmol), and formic acid (1 mL) in methanol (20 mL). The solution was stirred vigorously for 5 minutes at which time the light yellow-brown solution became dark red, and a light orange-red solid precipitated from solution. The solid was collected by filtration through a glass frit, washed twice with cold methanol (−20° C.), and dried under vacuum to yield 22 g (98%). $^1$H NMR (CD$_2$Cl$_2$): δ1.27 (d, 12H, J$_{HH}$=6.72 Hz), 3.11 (septet, 2H, J$_{HH}$=6.72 Hz), 6.93 (t, 6H, J$_{HH}$=7.92 Hz), 7.04 (d, 1H, J$_{HH}$=7.92 Hz), 7.15 (d, 1H, J$_{HH}$=11.0 Hz) 7.29 (br s, 3H), 8.40 (s, 1H); $^{13}$C NMR (CD$_2$Cl$_2$): δ23.5, 28.4, 118.1, 118.3, 119.1, 123.2, 123.4, 126.0, 139.2, 145.4, 145.6, 149.7, 145.6, 167.1.

EXAMPLE XVII

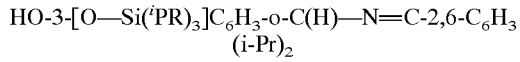
HO-3-[O—Si($^i$PR)$_3$]C$_6$H$_3$-o-C(H)—N=C-2,6-C$_6$H$_3$(i-Pr)$_2$ In a Schlenk flask under an atmosphere of N$_2$ was dissolved the compound of Example XVI (3.0 g, 10 mmol), triisopropylsilylchloride (2.3 g, 12 mmol), and imidazole (0.96 g, 14 mmol) in DMF (40 mL). The reaction was stirred at room temperature for 4 hours. After this time, Et$_2$O (250 mL) was added, and the solution was washed twice with water (2×100 mL). The Et$_2$O layer was dried with Na$_2$SO$_4$ and concentrated on a rotary evaporator to a yellow-orange oil. The oil was loaded onto a silica gel column and eluted with 95:5 hexane:ethyl acetate. Removal of solvent yielded 4.1 g (89%) of an orange oil. $^1$H NMR (C$_6$D$_6$): δ0.99 (d, 12H, J$_{HH}$=6.86 Hz), 1.15 (d, 18H, J$_{HH}$=6.83 Hz), 1.29 (septet, 3H, J$_{HH}$=6.83 Hz), 2.93 (septet, 2H, J$_{HH}$=6.86 Hz), 6.59–7.11 (m, 6H), 7.89 (s, 1H), 13.44 (s, 1H); $^{13}$C NMR (C$_6$D$_6$): δ20.4, 23.5, 26.7, 28.4, 118.5, 119.8, 123.5, 123.8, 124.9, 125.8, 130.1, 133.4, 135.9, 138.8, 144.8, 153.5, 167.4.

EXAMPLE XVIII

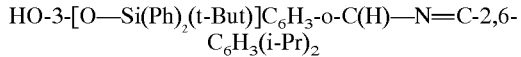
HO-3-[O—Si(Ph)$_2$(t-But)]C$_6$H$_3$-o-C(H)—N=C-2,6-C$_6$H$_3$(i-Pr)$_2$ In a Schlenk flask under an N$_2$ atmosphere was dissolved the compound of Example XVI (3.0 g, 10 mmol), diphenyl-t-butylsilylchloride (3.3 g, 12 mmol), and imidazole (0.96 g, 14 mmol) in DMF (40 mL). The reaction was stirred at room temperature for 4 hours. After this time, Et$_2$O (250 mL) was added and the solution was washed twice with distilled water (2×100 mL). The Et$_2$O layer was dried with Na$_2$SO$_4$ and concentrated on a rotary evaporator to a yellow-orange oil. The oil was loaded onto a silica gel column and eluted with 90:10 hexane:ethyl acetate. Removal of solvent yielded 4.4 g (83%) of an orange oil. $^1$H NMR (C$_6$D$_6$): δ0.98 (d, 12H,J$_{HH}$=6.84 Hz), 1.26 (s, 9H), 2.90 (septet, 2H, J$_{HH}$=6.84 Hz), 6.28 (t, 1H, J$_{HH}$=7.77 Hz), 6.47 (d, 1H, J$_{HH}$=7.77 Hz), 6.82 (d, 1H, J$_{HH}$=7.92 Hz), 7.10 (m, 3H), 7.87 (m, 1H), 13.49 (s, 1H); $^{13}$C NMR (C$_6$D$_6$): δ13.3, 18.2, 23.4, 28.5, 118.8, 119.8, 123.5, 124.1, 124.9, 125.8, 138.8, 145.4, 146.9, 153.7, 167.4.

EXAMPLE XIX

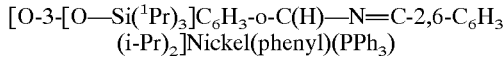
[O-3-[O—Si($^i$Pr)$_3$]C$_6$H$_3$-o-C(H)—N=C-2,6-C$_6$H$_3$(i-Pr)$_2$]Nickel(phenyl)(PPh$_3$)

In a Schlenk flask was dissolved the Na salt of the product of Example XVII (0.70 g, 1.3 mmol) and bis(triphenylphosphine)nickel(phenyl)chloride (1.0 g, 1.4 mmol) in benzene (30 mL). The reaction of was stirred at room temperature for 30 minutes. After this time, the reaction was filtered by cannula filtration, and the filtrate was concentrated in vacuo to ~5 mL. Pentane (30 mL) was added and the reaction was cooled to −78° C. and stored at this temperature for 2 days. A yellow-orange solid precipitated from solution, and was isolated by cannula filtration to yield 0.70 g (57%) of a waxy, yellow-orange solid. $^1$H NMR (C$_6$D$_6$): δ0.84 (br s, 18H), 1.09 (d, 6H, J$_{HH}$=7.32 Hz), 1.21 (d, 6H, J$_{HH}$=7.32 Hz), 4.20 (septet, 2H, J$_{HH}$=7.32 Hz), 6.15–7.80 (m, 30H), 7.97 (d, 1H, J$_{HP}$=8.72 Hz); $^{13}$C NMR (C$_6$D$_6$): δ13.0, 18.0, 22.8, 25.5, 28.9, 113.1, 120.4, 120.7, 121.0, 122.7, 125.0, 125.9, 126.2, 129.5, 132.4, 132.8, 134.1, 134.8 (d, J$_{CP}$=9.76 Hz), 136.7, 138.0, 140.7, 149.2, 150.0, 159.0, 166.0; $^{31}$P NMR (C$_6$D$_6$): δ23.13.

EXAMPLE XX

[O-3-[O—Si(Ph)$_2$(t-Bu)]C$_6$H$_3$-o-C(H)—N=C-2,6-C$_6$H$_3$(i-Pr)$_2$Nickel(phenyl)(PPh$_3$)

In a Schlenk flask was dissolved the Na salt of the compound of Example XVIII (0.81 g, 1.3 mmol) and bis(triphenylphosphine)nickel(phenyl)chloride (1.0 g, 1.4 mmol) in benzene (30 mL). The reaction was stirred at room temperature for 1.5 hours. After this time, the reaction was filtered by cannula filtration, and the filtrate was concentrated in vacuo to ~5 mL. Pentane (30 mL) was added with vigorous stirring, and the reaction was cooled to −25° C. A yellow-orange solid precipitated from solution, and was isolated by cannula filtration to yield 0.92 g (68%) of a yellow-orange solid. $^1$H NMR (C$_6$D$_6$): δ0.52 (s, 9H), 1.05 (d, 6H,J$_{HH}$=6.60 Hz), 1.21 (d, 6H, J$_{HH}$=6.60 Hz), 4.12 (septet, 2H,J$_{HH}$=6.60 Hz), 6.18–7.75 (m, 40H), 7.94 (d, 1H, J$_{HP}$=9.16 Hz); $^{13}$C NMR (C$_6$D$_6$): δ18.8, 22.7, 25.5, 26.3, 28.8, 99.8, 113.1, 120.5, 121.1, 122.5, 122.9, 125.0, 126.2, 127.5, 129.6, 130.0, 132.5, 133.6, 134.9 (d, J$_{CP}$=9.76 Hz), 135.7, 136.7, 140.8, 148.6, 150.0, 155.6, 158.8, 159.1, 166.2; $^{31}$P NMR (C$_6$D$_6$): δ22.78. Anal. Calcd for C$_{59}$H$_{60}$NNiO$_2$PSi: C, 75.96; H, 6.48; N, 1.50; Found: C, 75.57; H, 6.74; N, 1.03.

EXAMPLE XXI

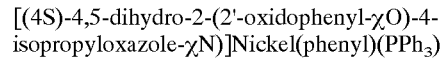
[(4S)-4,5-dihydro-2-(2'-oxidophenyl-χO)-4-isopropyloxazole-χN)]Nickel(phenyl)(PPh$_3$)

In a Schlenk flask was dissolved the Na salt of (4S)-4,5-dihydro-2-(2'-hydroxyphenyl)-4-isopropyloxazole (470 g, 1.6 mmol) and bis(triphenylphosphine)nickel(phenyl) chloride (1.0 g, 1.4 mmol) in benzene (20 mL). The reaction was stirred at room temperature for 1.5 hours. After this time, the reaction was filtered by cannula filtration, and the filtrate was concentrated in vacuo to ~3 mL. Pentane (30 mL) was added with vigorous stirring and the reaction was cooled to −78° C. A yellow-orange solid precipitated from solution, and was isolated by cannula filtration to yield 0.54 g (62%) of a yellow-orange solid. $^1$H NMR (C$_6$D$_6$): δ0.24 (d, 3H, J$_{HH}$=8.80 Hz), 0.63 (d, 3H,J$_{HH}$=8.80 Hz), 2.24 (septet, 1H, J$_{HH}$=8.80 Hz), 2.92 (d of d, 1H, J$_{HH}$=8.32 Hz, J$_{HH'}$=2.92 Hz), 3.36 (t, 1H, J$_{HH}$=8.80 Hz), 3.64 (d of d, 1H, J$_{HH}$=8.32 Hz, J$_{HH'}$=2.92 Hz), 6.09–7.73 (m, 29H); $^{13}$C NMR (C$_6$D$_6$): δ68.0, 74.2, 109.3, 113.1, 121.6, 122.5, 122.6, 126.3, 127.4, 127.8, 127.9, 128.3, 128.6, 129.6, 131.1, 131.5, 133.5, 133.7, 133.9, 134.5 (d, J$_{CP}$=10.4 Hz), 143.4, 149.1, 149.5, 166.5, 168.8; $^{31}$P NMR (C$_6$D$_6$): δ28.88.

EXAMPLE XXII

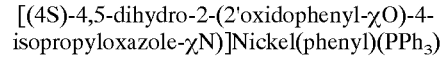
[(4S)-4,5-dihydro-2-(2'oxidophenyl-χO)-4-isopropyloxazole-χN)]Nickel(phenyl)(PPh$_3$)

In a Schlenk flask was dissolved the Na salt of (4S)-4,5-dihydro-2-(2'-hydroxyphenyl)-4-isopropyloxazole (530 g, 1.6 mmol) and bis(triphenylphosphine)nickel(phenyl) chloride (1.0 g, 1.4 mmol) in benzene (20 mL). The reaction was stirred at room temperature for 1.5 hours. After this time, the reaction was filtered by cannula filtration, and the filtrate was concentrated in vacuo to ~5 mL. Pentane (30 mL) was added with vigorous stirring, and the reaction was cooled to −78° C. A yellow-orange solid precipitated from solution, and was isolated by cannula filtration to yield 0.71 g (78%) of a yellow-orange solid. $^1$H NMR (C$_6$D$_6$): δ4.13 (d of d, 1H, $J_{HH}$=8.32 Hz, $J_{HH}$=8.32 Hz), 4.22 (d of d, 1H, $J_{HH}$=8.32 Hz, $J_{HH}$=8.32 Hz), 4.43 (t, 1H, $J_{HH}$=8.32 Hz), 6.09–7.73 (m, 29H); $^{13}$C NMR (C$_6$D$_6$): δ68.0, 74.2, 109.3, 113.1, 121.6, 122.5, 122.6, 126.3, 127.4, 127.8, 127.9, 128.3, 128.6, 129.6, 131.1, 131.5, 133.5, 133.7, 133.9, 134.5 (d, $J_{CP}$=10.4 Hz), 143.4, 149.1, 149.5, 166.5, 168.8; $^{31}$P NMR (C$_6$D$_6$): δ28.01. Anal. Calcd for C$_{39}$H$_{32}$NNiO$_2$P: C, 73.61; H, 5.07; N, 2.20. Found: C, 73.77; H, 5.24; N, 2.23.

EXAMPLE XXIII

HO-5-(OMe)C$_6$H$_3$-o-C(H)=N-2,6-C$_6$H$_3$(i-Pr)$_2$

To a methanol (25 mL) solution of 4-methoxysalicylaldehyde (10 g, 66 mmol) was added formic acid (1.0 mL) and 2,6-diisopropylaniline (15 g, 65 mmol). The resulting mixture was stirred at room temperature for 1 hour. After this time, the solution was stored at −25° C. for 24 hours. Yellow crystals precipitated from solution. The crystals were filtered and washed with −25° C. methanol (2×20 mL) to yield 15 g (72%) of a yellow solid. $^1$H NMR (C$_6$D$_6$): δ1.07 (d, 12H, $J_{HH}$=8.56 Hz), 2.98 (septet, 2H, $J_{HH}$=8.56 Hz), 3.29 (s, 3H), 6.60–7.16 (m, 6H), 7.86 (s, 1H), 12.89 (s, 1H); $^3$C NMR (C$_6$D$_6$): δ23.5, 28.5, 55.3, 115.8, 118.7, 120.7, 123.5, 125.8, 138.7, 147.1, 152.7, 156.2, 167.

EXAMPLE XXIV

HO-5-(NO$_2$)C$_6$H$_3$-o-C(H)=N-2,6-C$_6$H$_3$(i-Pr)$_2$

To a methanol (15 mL) solution of 4-nitrosalicylaldehyde (10 g, 60 mmol) was added formic acid (1.0 mL) and 2,6-diisopropylaniline (13 g, 75 mmol). The resulting mixture was stirred at room temperature for 10 minutes. After this time, yellow crystals precipitated from the solution. The crystals were filtered and washed with methanol (2×20 mL) to yield 15 g (96%) of a yellow solid. $^1$H NMR (CD$_2$Cl$_2$): δ1.19 (d, 12H, $J_{HH}$=6.85 Hz), 2.96 (septet, 2H, $J_{HH}$=6.85 Hz), 7.14 (d, 1H, $J_{HH}$=9.18 Hz), 7.23 (br s, 3H), 8.30 (d, 1H, $J_{HH}$=9.18 Hz), 8.40 (s, 1H), 8.43 (s, 1H), 14.30 (s, 1H); $^{13}$C NMR (CD$_2$Cl$_2$): δ23.6, 28.6, 118.6, 123.8, 126.6, 128.7, 128.8, 133.1, 139.1, 140.9, 145.2, 166.0, 167.4.

EXAMPLE XXV

HO-3,5-Cl$_2$C$_6$H$_2$-o-C(H)=N-2,6-C$_6$H$_3$(i-Pr)$_2$

To a methanol (15 mL) solution of 4,6-dichlorosalicylaldehyde (10 g, 52 mmol) was added formic acid (1.0 mL) and 2,6-diisopropylaniline (12 g, 65 mmol). The resulting mixture was stirred at room temperature for 10 minutes. After this time, yellow crystals precipitated from the solution. The crystals were filtered and washed with methanol (2×20 mL) to yield 17 g (95%) of a yellow solid. $^1$H NMR (C$_6$D$_6$): δ0.98 (d, 12H, $J_{HH}$=6.88 Hz), 2.77 (septet, 2H, $J_{HH}$=6.88 Hz), 6.60–7.11 (m, 5H), 7.47 (s, 1H), 14.02 (s, 1H); $^{13}$C NMR (C$_6$D$_6$): δ23.2, 28.2, 119.6, 123.1, 123.2, 123.3, 126.2, 129.7, 132.9, 138.3, 145.4, 156.3, 165.5.

EXAMPLE XXVI

[O-5-(OMe)C$_6$H$_3$-o-C(H)=N-2,6-C$_6$H$_3$(i-Pr)$_2$] Nickel(phenyl)(PPh$_3$)

In a Schlenk flask was dissolved the Na salt of the product from Example XXII (0.64 g, 1.6 mmol) and bis (triphenylphosphine)nickel(phenyl)chloride (1.0 g, 1.4 mmol) in benzene (20 mL). The reaction was stirred at room temperature for 1 hour. After this time, the reaction was filtered by cannula filtration, and the filtrate was concentrated in vacuo to ~5 mL. Pentane (30 mL) was added to the vigorously stirred solution, which was then cooled to −78° C. A yellow-orange solid precipitated from solution, and was isolated by cannula filtration to yield 0.88 g (86%) of a yellow-orange solid. $^1$H NMR (C$_6$D$_6$): δ1.08 (d, 6H, $J_{HH}$=6.84 Hz), 1.30 (d, 6H, $J_{HH}$=6.84 Hz), 3.31 (s, 3H), 4.09 (septet, 2H, $J_{HH}$=6.84 Hz), 3.29 (s, 3H), 6.32–7.69 (m, 40H), 7.88 (d, 1H, $J_{HP}$=9.28 Hz); $^{13}$C NMR (C$_6$D$_6$): δ22.6, 25.6, 28.8, 55.4, 113.1, 117.6, 121.2, 122.6, 123.7, 125.0, 125.2, 126.0, 129.4, 131.6, 132.0, 134.5 (d, $J_{CP}$=9.76 Hz), 138.2, 140.6, 149.4, 150.4, 161.9, 165.7; $^{31}$P NMR (C$_6$D$_6$): δ24.63, Anal. Calcd for C$_{44}$H$_{44}$NNiO$_2$P: C, 74.59; H, 6.26; N, 1.98. Found: C, 74.01; H, 6.20; N, 1.65.

EXAMPLE XXVII

[O-5-(NO$_2$)C$_6$H$_3$-o-C(H)=N-2,6-C$_6$H$_3$(i-Pr)$_2$] Nickel(phenyl)(PPh$_3$)

In a Schlenk flask was dissolved the Na salt of the compound of Example XXIV (0.56 g, 1.6 mmol) and bis(triphenylphosphine)nickel(phenyl)chloride (1.0 g, 1.4 mmol) in benzene (20 mL). The reaction was stirred at reflux for 1 hour. After this time, the reaction was filtered by cannula filtration, and the filtrate was concentrated in vacuo to ~5 mL. Pentane (30 mL) was added to the vigorously stirred solution. A light-green solid precipitated from solution, and was isolated by cannula filtration to yield 0.84 g (89%) of a yellow-orange solid. $^1$H NMR (C$_6$D6): δ0.96 (d, 6H, $J_{HH}$=6.96 Hz), 1.22 (d, 6H, $J_{HH}$=6.96 Hz), 3.89 (septet, 2H, $J_{HH}$=6.96 Hz), 5.91–7.90 (m, 30H), 8.06 (d, 1H, $J_{HP}$=2.92 Hz); $^{13}$C NMR (C$_6$D$_6$): δ22.2, 25.5, 28.7, 118.4, 121.4, 122.4, 122.6, 123.3, 125.2, 126.1, 128.0, 128.3, 129.9, 130.4, 130.9, 131.7, 134.2 (d, $J_{CP}$=9.91 Hz), 137.5, 140.1, 149.0, 165.8, 170.5; $^{13}$P NMR (C$_6$D$_6$): δ25.51.

EXAMPLE XXVIII

[O-3,5-Cl$_2$C$_6$H$_2$-o-C(H)=N-2,6-C$_6$H$_3$(i-Pr)$_2$]Nickel (phenyl)(PPh$_3$)

In a Schlenk flask was dissolved the Na salt of the compound of example XXV (0.66 g, 1.5 mmol) and bis (triphenylphosphine)nickel(phenyl)chloride (1.0 g, 1.4 mmol) in benzene (20 mL). The reaction was stirred at room temperature for 1 hour. After this time, the reaction was filtered by cannula filtration, and the filtrate was concentrated in vacuo to ~5 mL. Pentane (30 mL) was added to the reaction. A yellow-orange solid precipitated from solution, and was isolated by cannula filtration to yield 0.91 g (74%) of a yellow-orange solid. $^1$H NMR (C$_6$D$_6$): δ0.98 (d, 6H, $J_{HH}$=6.80 Hz), 1.22 (d, 6H, $J_{HH}$=6.80 Hz), 3.92 (septet, 2H, $J_{HH}$=6.80 Hz), 6.25–7.67 (m, 30H); $^{13}$C NMR (C$_6$D$_6$): δ22.6, 25.5, 28.8, 117.4, 120.0, 122.8, 125.3, 126.2, 128.3, 128.6, 129.7, 130.5, 131.0, 131.5, 133.3, 133.8, 134.0, 134.4 (d, $J_{CP}$=9.77 Hz), 137.4, 140.1, 149.4, 159.6, 165.2; $^{31}$P NMR (C$_6$D$_6$): δ25.93. Anal. Calcd for C$_{43}$H$_{40}$Cl$_2$NNiOP: C, 69.29; H, 5.41; N, 1.88. Found: C, 69.87; H, 5.74; N, 1.63.

EXAMPLE XXIX p-Trifluoromethylsalicylaldehyde

To a solution of p-trifluoromethylphenol (7.1 g, 44 mmol) and 2,6-lutidine (1.9 g, 17.6 mmol) in toluene (80 mL) was slowly added SnCl$_4$ (1.2 g, 4.4 mmol). The solution was stirred at room temperature for 20 minutes. Paraformaldehyde was added (3.2 g, 106 mmol) and the reaction was stirred at 110° C. for 12 hours. After cooling to room temperature, the reaction mixture was poured into water (250 mL), and adjusted to pH 1 with concentrated HCl. The mixture was extracted with diethyl ether (500 mL), and the organic layer was washed twice with saturated brine and dried over Na$_2$SO$_4$. The solvent was removed by rotary evaporation to leave a yellow oil. The oil was loaded onto a silica gel column and eluted with 6:1 hexane:ethyl acetate. The yield of product was 1.0 g (12%). $^1$H NMR(CDCl$_3$): δ7.21–7.91 (m, 12H), 9.91 (s, 1H), 11.32 (s, 1H).

EXAMPLE XXX

HO-5-(CF$_3$)C$_6$H$_2$-o-C(H)=N-2,6-C$_6$H$_3$(i-Pr)$_2$

To a methanol (10 mL) solution of 5-trifluoromethylsalicylaldehyde (0.7 g, 4.1 mmol) was added formic acid (0.5 mL) and 2,6-diisopropylaniline (0.8 g, 4.5 mmol). The resulting mixture was stirred at room temperature for 15 minutes. After this time, it was kept at −80° C. for 1 hour, yellow crystals precipitated from the solution. The crystals were filtered, dried under vacuum to yield 1.2 g (85%) of a yellow solid. $^1$H NMR (C$_6$D$_6$): δ1.04 (d, 12H), 2.85 (septet, 2H, J$_{HH}$=6.88 Hz), 6.85–7.25 (m, 5H), 7.61 (s, 1H), 13.82 (s, 1H).

EXAMPLE XXXI

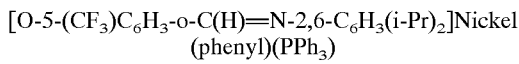
[O-5-(CF$_3$)C$_6$H$_3$-o-C(H)=N-2,6-C$_6$H$_3$(i-Pr)$_2$]Nickel(phenyl)(PPh$_3$)

In a Schlenk flask was dissolved the Na salt of Example XXX (0.4 g, 0.6 mmol) and bis(triphenylphoshine)nickel(phenyl)chloride 0.46g, 0.6 mmol) in benzene (15 mL). The reaction was stirred at room temperature for 1 hour. After this time, the reaction was filtered by cannula filtration, and the filtrate was concentrated in vacuo to ~2 mL. Pentane (20 mL) was added to the vigorously stirred solution, which was then cooled to −78° C. A yellow-orange solid precipitated from solution, and was isolated by cannula filtration to yield 0.6 g (65%) of a yellow-orange solid. $^1$H NMR(C$_6$D$_6$): δ0.95 (d, 6H, J$_{HH}$=6.84 Hz), 1.20 (d, 6H, J$_{HH}$=6.84 Hz), 3.95 (septet, 2H, J$_{HH}$=6.84 Hz), 6.32–7.81 (m, 40H, 31p NMR (C$_6$D$_6$): δ26.10.

EXAMPLE XXXII

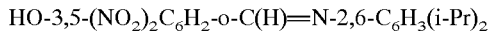
HO-3,5-(NO$_2$)$_2$C$_6$H$_2$-o-C(H)=N-2,6-C$_6$H$_3$(i-Pr)$_2$ 3,5-dinitrosalicylaldehyde was converted to the corresponding salicylaldimine by reaction with 2,6-diisopropylaniline according to the general procedure of Example XXIV. The yield of the 3,5-dinitrosalicylaldimine compound was 70%.

EXAMPLE XXXIII

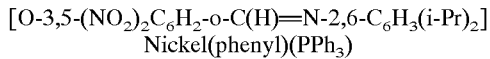
[O-3,5-(NO$_2$)$_2$C$_6$H$_2$-o-C(H)=N-2,6-C$_6$H$_3$(i-Pr)$_2$]Nickel(phenyl)(PPh$_3$)

The product of Example XXXII was reacted with bis(triphenylphosphine)nickel(phenyl)chloride according to the general procedure of Example XXVII. The yield of the 3,5-dinitrosalicylaldimine nickel (II) complex was 58%.

EXAMPLE XXXIV

General Procedure for Nitration of 3-R$^1$-Salicylaldehydes

To a solution of 5 mmol of the 3-R$^1$-salicylaldehyde in 10 ml of glacial acetic acid is added at room temperature 1 or 2 equivalents of concentrated HNO$_3$. After stirring for 40 minutes at room temperature, the mixture is poured into 100 ml of water. The yellow precipitate is collected by vacuum filtration, washed with water and dried in vacuo.

Using this procedure, the following 3-R$^1$-salicylaldehydes were nitrated (yield of nitration product in parentheses): 6-t-butylsalicylaldehyde (82%), 6-phenylsalicylaldehyde (71%), and 2-(9-anthracene)salicylaldehyde from Example XII (88% for mono-nitration at the 10-position of anthracene, 64% for di-nitration at the 10 position of the anthracene and para-position of the salicylaldehyde ring).

EXAMPLE XXXV

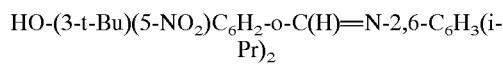
HO-(3-t-Bu)(5-NO$_2$)C$_6$H$_2$-o-C(H)=N-2,6-C$_6$H$_3$(i-Pr)$_2$

The nitrated product of t-butylsalicylaldehyde prepared according to the general procedure of Example XXXIV was converted to the imine by condensation with 2,6-diisopropylaniline using a procedure analogous to Example III. The yield of the imine derivative was 63%.

EXAMPLE XXXVI

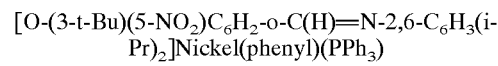
[O-(3-t-Bu)(5-NO$_2$)C$_6$H$_2$-o-C(H)=N-2,6-C$_6$H$_3$(i-Pr)$_2$]Nickel(phenyl)(PPh$_3$)

The Na salt of the product from Example XXXV was reacted with bis(triphenylphosphine)nickel(phenyl)chloride according to a procedure analogous to Example V. The yield of the salicylaldimine nickel (II) complex was 40%.

EXAMPLE XXXVII

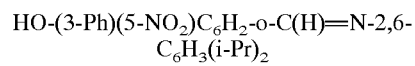
HO-(3-Ph)(5-NO$_2$)C$_6$H$_2$-o-C(H)=N-2,6-C$_6$H$_3$(i-Pr)$_2$

The nitrated product of 6-phenylsalicylaldehyde prepared according to the general procedure of Example XXXIV was converted to the corresponding imine by condensation with 2,6-diisopropylaniline using a procedure analogous to Example IV. The yield of the imine derivative was 83%.

EXAMPLE XXXVIII

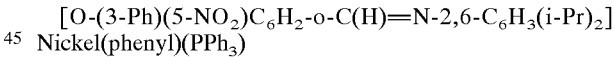
[O-(3-Ph)(5-NO$_2$)C$_6$H$_2$-o-C(H)=N-2,6-C$_6$H$_3$(i-Pr)$_2$]Nickel(phenyl)(PPh$_3$)

The Na salt of the product from Example XXXVII was reacted with bis(triphenylphosphine)nickel(phenyl)chloride according to a procedure analogous to Example VI. The yield of the salicylaldimine nickel (II) complex was 77%.

EXAMPLE XXXVIX

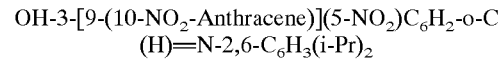
OH-3-[9-(10-NO$_2$-Anthracene)](5-NO$_2$)C$_6$H$_2$-o-C(H)=N-2,6-C$_6$H$_3$(i-Pr)$_2$ The di-nitrated product of 2-(anthracene)salicylaldehyde (see Example XII for synthesis of this aldehyde), prepared according to the general procedure of Example XXXIV, was converted to the corresponding imine by condensation with 2,6-diisopropylaniline using a procedure analogous to Example XIII. The yield of the imine derivative was 66%.

EXAMPLE XL

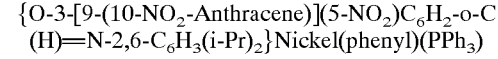
{O-3-[9-(10-NO$_2$-Anthracene)](5-NO$_2$)C$_6$H$_2$-o-C(H)=N-2,6-C$_6$H$_3$(i-Pr)$_2$}Nickel(phenyl)(PPh$_3$)

The Na salt of the product from Example XXXVIX was reacted with bis(triphenylphosphine)nickel(phenyl)chloride according to a procedure analogous to Example XIV. The yield of the salicylaldimine nickel (II) complex was 72%.

EXAMPLE XLI

HO-3-[9-(10-NO$_2$-Anthracene)]C$_6$H$_3$-o-C(H)=N-2, 6-C$_6$H$_3$(i-Pr)$_2$

The mono-nitrated product of 2-(anthracene) salicylaldehyde (see Example XII for synthesis of this aldehyde), prepared according to the general procedure of Example XXXII, was converted to the corresponding imine by condensation with 2,6-diisopropylaniline using a procedure analogous to Example IX. The yield of the imine derivative was 70%.

EXAMPLE XLII

{O-3-[9-(10-NO$_2$-Anthracene)]C$_6$H$_3$-o-C(H)=N-2, 6-C$_6$H$_3$(i-Pr)$_2$}Nickel(phenyl)(PPh$_3$)

The Na salt of the product from Example XLI was reacted with bis(triphenylphosphine)nickel(phenyl)chloride according to a procedure analogous to Example XIV. The yield of the salicylaldimine nickel (II) complex was 70%.

EXAMPLE XLIII

HOC$_{10}$H$_6$-o-C(H)=N-2,6-C$_6$H$_3$(i-Pr)$_2$

To a solution of 5.75 of 2-hydroxynaphthaldehyde and 7.6 mL of 2,6-diisopropylaniline in 100 mL of benzene was added 0.32 g of p-toluenesulfonic acid. The mixture was heated at reflux using a Dean-Stark trap for 16 hours. After cooling to room temperature, the solvent is evaporated on a rotary evaporator. Upon addition of 30 mL of methanol to the residue, an orange precipitate was formed. The precipitate was filtered and dried in vacuo. The yield of orange solid was 85%.

EXAMPLE XLIV

[OC$_{10}$H$_6$-o-C(H)=N-2,6-C$_6$H$_3$(i-Pr)$_2$]Nickel(phenyl)(PPh$_3$)

The Na salt of the product of Example XLIII was prepared by reaction of the product of Example XLIII (2.0 g) in 60 mL of THF with 0.30 g of NaH. The mixture was stirred for 1 hour at room temperature. After filtration of the reaction solution through a frit filter containing Celite, the solvent was evaporated. The yield of Na salt was 97%.

To a mixture of 0.49 g of the Na salt of the product of Example XLIII and 0.96 g of bis(triphenylphosphine)nickel (phenyl)chloride was added at room temperature 30 mL of benzene. After stirring at room temperature for 5 hours, the mixture was filtered (frit with Celite) and the volume of the dark red solution was reduced in vacuo to ~3 mL. Pentane (30 mL) was added and the mixture was cooled to −50° C. An orange precipitate was formed. The precipitate was filtered and dried in vacuo. The yield of orange solid was 75%.

EXAMPLE XLV

Some of the above late transition metal salicylaldimine late transition metal chelates were used in the catalytic polymerization of ethylene according to the following general procedure: The catalyst, in amounts indicated in the below table, was weighed and placed into a pressure container under an atmosphere of nitrogen. The pressure container was then evacuated and backfilled with ethylene. 80 mL of dry toluene was then cannula transferred into the pressure container followed by addition of 5 mL of a toluene solution containing the phosphine sponge adjunct, bis (cyclooctadiene-nickel[Ni(COD)$_2$] or tris (pentafluorophenyl)boron[(B(C$_6$F$_5$)$_3$]. The ethylene pressure was raised to that indicated in Table 1 below and maintained at the prescribed pressure. The indicated temperature was the initial temperature of the reactor. In all reactions (except those run at 0° C.) the temperature was allowed to rise due to the reaction exotherm. The reaction was run with stirring for forty minutes. The polymerization process was terminated and 500 mL of methanol was added to the toluene solution to precipitate the polyethylene product. The polyethylene was collected by filtering the material through a glass frit filter. The number of branches of C$_1$+C$_2$+C$_3$+C$_4$ and higher of the polymer was estimated using $^{13}$C NMR analysis of the resultant polymer in hot 1,3,5-trichlorobenzene. Polymer molecular weight was determined by gel permeation chromatography in trichlorobenzene at 135° C. and is relative to broad polyethylene calibration standards.

EXAMPLE XLVI

OH-3-(9-Anthracene)C$_6$H$_3$-o-C(H)=N-2,6-C$_6$H$_2$(i-Pr)$_2$(4-NO$_2$)

The 3-(anthracene)salicyladehyde was converted to the corresponding imine by condensation with 2,6-diisopropyl-4-nitroaniline using a procedure analogous to Example XIII. The yield of the imine derivative was 81%.

EXAMPLE XLVII (O-3-(9-Anthracene)C$_6$H$_3$-o-C(H)=N-2,6-C$_6$H$_2$(i-Pr)$_2$(4-NO$_2$))Nickel(phenyl)(PPh$_3$)

In a Schlenk flask was dissolved the Na salt of the product of Example XLVI (1.44 g, 2.15 mmol) and bis (triphenylphosphine)nickel(phenyl)chloride (1.45 g, 2.08 mmol) in benezene (25 mL). The reaction was stirred at room temperature for 16 hours. After this time the reaction was evaporated, the residue extracted with methylene chloride (25 mL), filtered by cannula filtration, and the filtrate was evaporated. The residue was washed with pentane (25 ml) and dried in vacuum to yield 1.00 g (52%) of an orange solid.

EXAMPLE XLVIII

OH-3-[9-(10-NO$_2$-Anthracene)](5-NO$_2$)C$_6$H$_2$-o-C(H)=N-2,6-C$_6$H$_2$(i-Pr)$_2$(4-NO$_2$)

The di-nitrated product of 3-(anthracene)salicyladehyde (see Example XII for synthesis of this aldehyde), prepared according to the general procedure of Example XXXIV, was converted to the corresponding imine by condensation with 2,6-diisopropyl-4-nitroaniline using a procedure analogous to Example XIII. The yield of the imine derivative was 50%.

EXAMPLE XLVIX (O-3-[9-(10-NO$_2$-Anthracene)](5-NO$_2$)C$_6$H$_2$-o-C(H)=N-2,6-C$_6$H$_2$(i-Pr)$_2$(4-NO$_2$))Nickel(phenyl)(PPh$_3$)

The Na salt of the product of Example XLVIII was reacted with bis(triphenylphosphine)nickel(phenyl)chloride according to a procedure analogous to Example XLVII. The yield of the salicylaldimine nickel (II) complex was 70%.

TABLE 1

Polymerization of Ethylene

| Cat. Ex. No. | [Cat] mM | Adjuct equiv. | Temp C.° | Press (psi) | Yield (g) | PDI[a] | Mw | Branches Total/1000 |
|---|---|---|---|---|---|---|---|---|
| II | 1.8 | $2^1$ | 25 | 80 | 2.0 | 1.54 | 4,000 | 45 |
| II | 1.8 | $2^1$ | 25 | 200 | 2.4 | 1.45 | 10,000 | 20 |
| V | 1.8 | $2^1$ | 25 | 80 | 8.0 | 2.25 | 26,000 | 55 |
| VI | 1.8 | $2^1$ | 25 | 80 | 20.0 | 2.28 | 23,300 | 40 |
| V | 0.9 | $2^1$ | 25 | 80 | 3.5 | 1.84 | 11,400 | 55 |
| VI | 0.9 | $2^1$ | 25 | 80 | 8.9 | 1.95 | 11,000 | 45 |
| V | 0.9 | $2^1$ | 0 | 80 | 3.1 | 3.10 | 6,600 | 25 |
| VI | 0.9 | $2^1$ | 0 | 80 | 3.9 | 2.45 | 108,000 | 10 |
| V | 0.9 | $2^1$ | 25 | 80 | 3.5 | 1.84 | 18,400 | 55 |
| V | 0.9 | $8^1$ | 25 | 80 | 4.8 | 2.34 | 43,200 | 40 |
| V | 0.9 | $1^2$ | 25 | 80 | 4.2 | 1.69 | 10,400 | 55 |
| V | 0.9 | $2^2$ | 25 | 80 | 3.3 | 2.55 | 11,000 | 45 |
| XIV[b] | 0.9 | $2^1$ | 25 | 80 | 7.0 | 3.85 | 37,700 | 30 |
| XIV[b] | 0.5 | $2^1$ | 25 | 80 | 0.8 | 2.30 | 56,700 | 5 |
| XIV[b] | 0.9 | $2^2$ | 25 | 80 | 7.0 | 6.84 | 49,500 | 35 |
| XIV[b] | 0.9 | $0.5^2$ | 25 | 80 | 5.0 | 3.63 | 42,500 | 20 |
| XIV[b] | 0.9 | — | 25 | 80 | 0.4 | 2.53 | 14,900 | 15 |
| XV[b] | 0.9 | $2^1$ | 25 | 80 | 7.4 | 6.43 | 54,000 | 0 |
| XV[b] | 0.9 | $2^2$ | 25 | 80 | 5.0 | 7.19 | 23,800 | 50 |
| XXVI[b] | 0.9 | $2^1$ | 25 | 80 | 1.0 | 1.68 | 7,300 | 39 |
| II[b] | 0.9 | $2^1$ | 25 | 80 | 2.0 | 1.54 | 4,000 | |
| XXVII[b] | 0.9 | $2^1$ | 25 | 80 | 8.0 | 18.0 | 143,000 | 32 |
| XXVIII[b] | 0.9 | $0.5^1$ | 25 | 80 | 1.5 | 3.28 | 22,500 | 9 |
| XXVII[b] | 0.5 | 1.0 | 25 | 80 | 3.0 | 18.0 | 366,000 | 12 |
| XXXI | 1.8 | $2^1$ | 25 | 80 | 0.9 | | | |
| XXXI | 0.9 | $2^2$ | 25 | 80 | 2.7 | | | |
| XXXIII | 1.8 | $2^1$ | 25 | 80 | 7.7 | | | |
| XXXVI | 0.9 | $2^1$ | 25 | 80 | 3.2 | | | ~25[c] |
| XXXVIII | 0.9 | $2^1$ | 25 | 80 | 7.0 | | | ~13[c] |
| XL | 0.9 | $2^1$ | 25 | 80 | 6.5 | | | ~20[c] |
| XL | 0.9 | $2^2$ | 25 | 80 | 9.7 | | | ~55[c] |
| XLII | 0.9 | $2^1$ | 25 | 80 | 4.0 | | | ~15[c] |
| XLII | 0.9 | $2^1$ | 25 | 80 | 3.3 | | | ~5[c] |
| XLII | 0.9 | $2^2$ | 25 | 80 | 7.0 | | | ~22[c] |
| XLIV | 0.5 | $2^2$ | 50 | 80 | 2.3 | | | |
| XLIV | 0.9 | $2^2$ | 25 | 80 | 2.3 | | | |
| XLIV | 0.9 | $2^1$ | 25 | 80 | 0.4 | | | |

[a]PDI = Polydispersity index, Mw/Mn
[b]Polymerization run 15 minutes
[c]Estimated from peak melting temperature on DSC scan.
[1]Adjunct used was Ni(COD)$_2$
[2]Adjunct used was B(C$_6$F$_5$)$_3$

EXAMPLE L

A series of polymerizations were carried out using nickel (II) salicylaldimine catalyst of the present invention, alone or, as part of a catalyst composition, in combination with a co-catalyst adjunct agent B(C$_6$F$_5$)$_3$ and/or a Lewis base. The procedures under which these polymerizations were conducted are outlined herein below and the specifics and results are given in the Tables which follow.

The salicylaldimine catalysts used are of compound I type wherein:

Catalyst "A": $R^1$ is 9-anthracenyl; $R^2$, X, $R^3$, and R are each hydrogen; $R^5$ is 2,6-diisopropylphenyl; $R^6$ is phenyl; L is triphenyl phosphine; A is oxygen and M is nickel.

Catalyst "B": $R^1$ is phenyl; $R^2$, X, $R^3$, and $R^4$ are each hydrogen; $R^5$ is 2,6-diisopropylphenyl; $R^6$ is phenyl; L is triphenyl phosphine; A is oxygen and M is nickel.

Catalyst "C": $R^1$ is 9-phenanthracenyl; $R^2$, X, $R^3$, and $R^4$ are each hydrogen; $R^5$ is 2,6-diisopropylphenyl; $R^6$ is phenyl; L is triphenyl phosphine; A is oxygen and M is nickel.

Catalyst "D": $R^1$ is hydrogen; $R^2$, X, $R^3$, and $R^4$ are each hydrogen; $R^5$ is 2,6-diisopropylphenyl; $R^6$ is phenyl; L is triphenyl phosphine; A is oxygen and M is nickel.

Catalyst "E": $R^1$ is 9-phenanthracenyl; $R^2$, $R^3$ and $R^4$ are each hydrogen; X is nitro; $R^5$ is 2,6-diisopropylphenyl; $R^6$ is phenyl; L is triphenyl phosphine; A is oxygen and M is nickel.

Catalyst "F": $R^1$ is phenyl; $R^2$, $R^3$ and $R^4$ are each hydrogen; X is nitro; $R^5$ is 2,6-diisopropylphenyl; $R^6$ is phenyl; L is triphenyl phosphine; A is oxygen and M is nickel.

Catalyst "G": $R^1$ is 10-nitroanthracenyl; $R^2$, $R^3$ and $R^4$ are each hydrogen; $R^5$ is 2,6-diisopropylphenyl; $R^6$ is phenyl; L is triphenyl phosphine; A is oxygen and M is nickel.

Catalyst "H": $R^1$ is 10-nitroanthracenyl; $R^2$, $R^3$, and $R^4$ are each hydrogen; $R^5$ is 2,6-diisopropyl-4-nitrophenyl; X is nitro; $R^6$ is phenyl; L is triphenyl phosphine; A is oxygen and M is nickel.

Catalyst "I": $R^1$ is anthracenyl; $R^2$, $R^3$ and $R^4$ are each hydrogen; $R^5$ is 2,6-diisopropyl-4-nitrophenyl; $R^6$ is phenyl; L is triphenyl phosphine; A is oxygen and M is nickel.

Catalyst "J": $R^1$ is 10-nitroanthracenyl; $R^2$, $R^3$ and $R^4$ are each hydrogen; X is nitro; $R^5$ is 2,6-diisopropylphenyl; $R^6$ is phenyl; L is triphenyl phosphine; A is oxygen and M is nickel.

(1) Polymerization with Catalyst Composition Containing Catalyst of Compound I with B(C6F$_5$)$_3$ as Co-catalyst Adjunct and Diethyl Ether as Lewis Base Additive The appropriate amount of Ni complex and co-catalyst adjunct were weighed into a 6 oz glass pressure bottle under an atmosphere of $N_2$. The solvent (generally 90 mL dry toluene) was then cannula transferred into the pressure bottle under a positive pressure of ethylene, followed by the specified amount of diethyl ether. The ethylene pressure was raised and maintained between 85 and 100 psig. When specified,-temperature control was accomplished by a water bath to control the exotherm. Stirring of the reaction mixture was maintained by a magnetic stirrer and stir bar. After completion of the polymerization reaction, methanol (1000 mL) and 1N hydrochloric acid (50 mL) was added to the toluene solution to precipitate the polymer and remove catalyst residue. The polyethylene product was collected by filtration through a glass frit, washed with methanol (100 mL) and dried under vacuum.

(2) Polymerization with Catalyst of Compound I without Co-catalyst Adjunct or Lewis Base Additive The appropriate amount of Ni complex was weighed into either a 6 or 12 oz. glass pressure bottle under an atmosphere of $N_2$. The solvent (90 mL) was then cannula transferred into the pressure bottle under a positive pressure of ethylene. The ethylene pressure was raised and maintained between 85 and 100 psig. When specified, temperature control was accomplished by a water bath to control the exotherm. Stirring of the polymerization mixture was maintained by a magnetic stirrer and stir bar. In cases where the viscosity of the polymerization mixture increased to the point where ethylene consumption slowed significantly, the pressure was released and additional amounts of solvent were added. Subsequently, the mixture was re-pressurized with ethylene. After completion of the polymerization reaction, methanol (1000 mL) and 1N hydrochloric acid (50 mL) was added to the toluene solution to precipitate the polymer and remove catalyst residue. The polyethylene product was collected by filtration through a glass frit, washed with methanol (100 mL) and dried under vacuum.

(3) Polymerization with Catalyst Composition Composed of Catalyst of Compound I with Different Lewis Base Additives The appropriate amount of Ni complex was weighed into either a 6 or 12 oz. glass pressure bottle under an atmosphere of $N_2$. The solvent (90 mL) was then cannula transferred into the pressure bottle under a positive pressure of ethylene, followed by the specified amount of additive. The ethylene pressure was raised and maintained between 85 and 100 psig. When specified, temperature control was accomplished by a water bath. Stirring of the polymerization mixture was maintained by a magnetic stirrer and stir bar. In cases where the viscosity of the polymerization mixture increased to the point where ethylene consumption slowed significantly, the pressure was released and additional amounts of solvent were added. Subsequently, the mixture was re-pressurized with ethylene. After completion of the polymerization reaction, methanol (1000 mL) and 1N hydrochloric acid (50 mL) was added to the toluene solution to precipitate the polymer and remove catalyst residue. The polyethylene product was collected by filtration through a glass frit, washed with methanol (100 mL) and dried under vacuum.

(4) Polymerizations Carried Out at Elevated Ethylene Pressure

A 1.5 liter Parr stainless steel reactor was charged with the appropriate amount of Ni complex, the specified volume of benzene, and diethyl ether in a dry box under an atmosphere of $N_2$. The reactor was assembled, removed from the dry box, and pressurized with ethylene (500 psig unless specified otherwise). The ethylene pressure was maintained between 490 and 500 psig unless specified otherwise. No temperature control was provided. Stirring of the reaction mixture was maintained by a magnetic stirrer and stir bar. After completion of the polymerization reaction, methanol (1000 mL) and 1N hydrochloric acid (50 mL) was added to the benzene solution to precipitate the polymer and remove catalyst residue. The polyethylene product was collected by filtration through a glass frit, washed with methanol (100 mL) and dried under vacuum.

(5) Copolymerizations with Functional Cyclic Olefins

The appropriate amount of Ni complex was weighed into a 12 oz. Fisher Porter pressure bottle under an atmosphere of argon in a dry box. A mechanical stirring assembly and thermocouple was attached, and the apparatus was removed from the dry box. The pressure bottle was evacuated, then back-filled with ethylene. Dry toluene (100 mL) was cannula transferred into a nitrogen-flushed stainless steel container fitted with a two-way valve. The container was then pressurized to 50 psig (unless specified otherwise) with ethylene. Dry diethyl ether (10 or 20 mL) was cannula transferred into another nitrogen-flushed stainless steel container fitted with two-way valve and the container was pressurized to 50 psig with ethylene. Into another stainless steel container fitted with two-way valve, a solution of functionalized monomer in a small volume of dry toluene was cannula transferred and the container was pressurized with ethylene to 50 psig. In rapid sequential fashion, the toluene, ether and solution of functionalized monomer, all under positive ethylene pressure (50 psig), were blown into the Fisher Porter bottle. A water bath (40–45° C.) was used to gently warm contents of the bottle. The bottle was pressurized to 50 psig with ethylene and maintained at 50 psig over the course of the copolymerization reaction. The reaction typically exothermed to a temperature between 45–55° C. When the uptake of ethylene became negligible, the ethylene pressure was released and the contents of the bottle were poured into 1 liter of methanol or acetone. The precipitated polymer was collected by vacuum filtration, re-suspended in a large volume of methanol, filtered, washed with fresh methanol and dried under vacuum.

TABLE 2

Polymerization of Ethylene with Catalyst Composition Containing Cocatalyst Adjunct and Lewis Base Additive.[a]

| Sample | Vol of $Et_2O$ (mL) | Catalyst | Temperature control | Catalyst Productivity (kg PE/mol Ni) | Yield PE (g) | $M_w$ | PDI | $T_m$ (° C.) | Total Branches[b] |
|---|---|---|---|---|---|---|---|---|---|
| 1 | 0.1 | A | no | 84.6 | 5.5 | 35,600 | 3.7 | 120 | 37 |
| 2 | 0.5 | A | no | 84.6 | 5.5 | 32,500 | 4.2 | 119 | 35 |
| 3 | 1 | A | no | 92.3 | 6.0 | 31,900 | 4.8 | 121 | 42 |
| 4 | 2 | A | no | 107.7 | 7.0 | 32,600 | 5.3 | 122 | 47 |
| 5 | 5 | A | no | 104.6 | 6.8 | 31,000 | 5.9 | 122 | 51 |
| 6 | 10 | A | no | 130.8 | 8.5 | 33,200 | 5.1 | 122 | 41 |

TABLE 2-continued

Polymerization of Ethylene with Catalyst Composition Containing Cocatalyst Adjunct and Lewis Base Additive.[a]

| Sample | Vol of Et$_2$O (mL) | Catalyst | Temperature control | Catalyst Productivity (kg PE/mol Ni) | Yield PE (g) | $M_w$ | PDI | $T_m$ (° C.) | Total Branches[b] |
|---|---|---|---|---|---|---|---|---|---|
| 7 | 20 | A | no | 103.1 | 6.7 | 33,000 | 6.0 | 125 | 40 |
| 8 | 90[e] | A | no | 69.2 | 4.5 | 57,000 | 2.8 | 123 | 32 |
| 9 | 5[f] | A | no | 57.5 | 3.9 | 78,200 | 2.0 | 129 | 6 |
| 10 | 5 | A | yes | 189.2 | 12.3 | 91,300 | 3.3 | 126 | 22 |
| 11 | 10[d] | A | yes | 424.6 | 27.6 | 172,000 | 2.7 | 126 | 13 |
| 12 | 90[c,d] | A | yes | 144.6 | 9.4 | 106,000 | 2.4 | 129 | 28 |
| 13 | 90[e] | B | yes | 103 | 6.8 | 15,900 | 2.2 | 85 | |

[a]All polymerizations reactions were carried out with 55 mg of Ni complex and 2 eq. of co-catalyst adjunct, B(C$_6$F$_5$)$_3$ in toluene (90 mL) at 80–90 psig of ethylene.
[b]Total number of C$_1$ + C$_2$ + C$_3$ + C$_4$ and higher branches per 1000 carbons.
[c]Diethyl ether used as only solvent.
[d]More solvent added during the reaction.
[e]THF used as only solvent.
[f]Ethyl vinyl ether used.

Table 2 essentially shows the use of Lewis base additive as part of catalyst compositions comprising a co-catalyst adjunct, B(C$_6$F$_5$)$_3$, with nickel (II) salicylaldimine catalyst. In total, the data show that catalyst productivity and polymer yield increase with increasing amount of diethyl ether. In entries where no temperature control was used, there does not appear to be a significant influence of the ether on the branching of the polyethylene produced (except ethyl vinyl ether). In instances where the polymerization reaction temperature was controlled, the data shows that catalyst productivity and polymer yield is further enhanced. Significantly, polymer molecular weight is increased and the molecular weight distribution (PDI) narrows when the temperature is controlled. Samples 8, 12 and 13 of Table 2 reveal that the catalyst is active when ether is present as solvent. Taken together, data in the table also indicate that the nickel salicylaldimine catalyst performs well with small or even large amounts of a Lewis base compound, such as ether.

TABLE 3

Polymerization of Ethylene Without Adjunct or Lewis Base Additive[a]

| Sample | Entry | Catalyst Productivity (kg PE/mol Ni) | Yield PE (g) | $M_w$ | PDI | $T_m$ (° C.) | Total Branches[b] |
|---|---|---|---|---|---|---|---|
| 14[c] | A | 842 | 55.1 | 77,300 | 6.2 | 120.8 | 23 |
| 15[c] | A | 1038 | 66.7 | 70,000 | 5.5 | 120.1 | 25 |
| 16 | E | 575 | 37.4 | 354,000 | 2.8 | 136.7 | 5 |
| 17 | F | 246 | 16.1 | 247,000 | 3.2 | 131.1 | 10 |
| 18 | H | 107 | 6.9 | 177,000 | 2.4 | 135.4 | 5 |
| 19 | G | 776 | 50.7 | 238,000 | 3.6 | 132.7 | 8 |
| 20 | I | 938 | 60.5 | 236,000 | 2.2 | 135.5 | 5 |
| 21 | J | 432 | 28.2 | 252,000 | 2.7 | 134.0 | 6 |
| 22 | B | 212 | 14.1 | 207,000 | 2.2 | 132.9 | 10 |
| 23 | C | 617 | 40.4 | 207,000 | 2.4 | 129.5 | 8 |

[a]All polymerizations reactions were carried out with 65 μmol of Ni complex in toluene (90 mL initially) at 80–90 psig of ethylene with temperature control.
[b]Total number of C$_1$ +C$_2$ + C$_3$ + C$_4$ and higher branches per 1000 carbons.
[c]More solvent added during the reaction.

Table 3 illustrates that nickel (II) salicylaldimine family of catalysts are active polymerization catalysts without any co-catalyst adjunct or Lewis base present. This demonstrates that this family of catalyst are true single-component polymerization catalysts.

TABLE 4

Polymerization of Ethylene with Catalyst "A" and Diethyl Ether as Additive.[a]

| Sample | Catalyst loading | Vol. of Et$_2$O (mL) | Catalyst Productivity (kg PE/mol Ni) | Yield PE (g) | $M_w$ | PDI | $T_m$ (° C.) | Total Branches[b] |
|---|---|---|---|---|---|---|---|---|
| 24 | 55 mg | 10[c] | 781.8 | 43.0 | 165,000 | 2.2 | 127 | 34 |
| 25 | 55 mg | 10[c] | 923.6 | 50.8 | 90,600 | 7.0 | 122 | 25 |
| 26 | 25 mg | 5[c,d] | 1220 | 30.5 | 62,800 | 5.5 | 120 | 28 |
| 27 | 10 mg | 5[c,d] | 430.0 | 4.3 | 193,000 | 2.0 | 132 | 10 |

[a]All polymerizations reactions were carried out in toluene (90 mL) at 80–90 psig of ethylene with temperature control.
[b]Total number of C$_1$ + C$_2$ + C$_3$ + C$_4$ and higher branches per 1000 carbons.
[c]More solvent added during the reaction.
[d]Only 50 mL of toluene used at the beginning of the reaction.

The significance of Table 4 is that it reveals that the subject catalyst is very active in the presence of an oxygenated Lewis base, such as ether. In comparison to Table 3 (catalyst A, samples 14 and 15), the catalyst productivity is shown to be similar. The data for catalyst "A" in Table 4, as compared to catalyst "A" in Table 3, show the benefit of Lewis base to the molecular weight of the polyethylene product. For catalyst A, polyethylene of higher molecular weight is generally produced when the catalyst composition is comprised of nickel (II) salicylaldimine catalyst and Lewis base.

Table 6 demonstrates that the subject catalyst is active in the presence of other Lewis base compounds. Notably, the catalyst remains active and produces high molecular PE even in the presence of water. Ziegler-Natta, metallocene catalysts and cationic nickel single site catalysts are generally not known to tolerate water.

TABLE 5

Polymerization of Ethylene with Catalyst A and Lewis Base Additives.[a]

| Sample | Additive | Additive Amount | Catalyst Productivity (kg PE/mol Ni) | Yield PE (g) | $M_w$ | PDI | $T_m$ (° C.) | Total Branches[b] |
|---|---|---|---|---|---|---|---|---|
| 28 | THF[c] | 10 mL | 467.3 | 25.7 | 270,000 | 2.4 | 133 | 5 |
| 29 | 1,4-Dioxane | 10 mL | 170.9 | 9.4 | 197,000 | 2.2 | 137 | 3 |
| 30 | Dimethoxyethane[c] | 10 mL | 1289 | 70.9 | 270,000 | 2.4 | 136 | 3 |
| 31 | Diglyme | 10 mL | 114.5 | 6.3 | 189,000 | 2.1 | 136 | 2 |
| 32 | Triglyme[c] | 10 mL | 663.6 | 36.5 | 218,000 | 2.2 | 134 | 4 |
| 33 | Tetraglyme[c] | 10 mL | 461.8 | 25.4 | 179,000 | 2.4 | 131 | 5 |
| 34 | Anisole | 10 mL | 45.5 | 2.5 | 184,000 | 2.6 | 139 | 4 |
| 35 | n-Butyl Ether | 15 mL | 58.2 | 3.2 | 184,000 | 2.3 | 135 | 4 |

[a]All polymerizations reactions were carried out with 55 mg of catalyst in toluene (90 mL) at 80–90 psig of ethylene with temperature control.
[b]Total number of $C_1 + C_2 + C_3 + C_4$ and higher branches per 1000 carbons.
[c]More toluene added during the reaction.

Table 5 shows that other members of the ether family also are effective Lewis base additives for the polymerization of ethylene when used with the subject catalyst. Dimethoxyethane appears to be most effective under the conditions used, as noted by the highest catalyst productivity and yield of PE. It should be noted that with temperature control, the catalyst/ether system produces highly linear polyethylene. The polymer produced is essentially high density polyethylene having a low amount of branching and high melting point. Note also that cyclic ethers as well as linear polyethers are effective additives.

TABLE 6

Polymerization of Ethylene with Catalyst "A" and Various Lewis Base Additives.[a]

| Sample | Additive | Additive Amount | Catalyst Productivity (kg PE/mol Ni) | Yield PE (g) | $M_w$ | PDI | $T_m$ (° C.) | Total Branches[b] |
|---|---|---|---|---|---|---|---|---|
| 36 | Acetone | 10 mL | 183.6 | 10.1 | 131,000 | 3.7 | 128 | 13 |
| 37 | Ethylacetate | 10 mL | 121.8 | 6.7 | 188,000 | 2.0 | 138 | |
| 38 | Ethanol | 10 mL | 12.7 | 0.7 | 46,600 | 3.0 | 129 | 17 |
| 39 | Water | 0.1 mL | 63.6 | 3.5 | 90,100 | 2.0 | 130 | 4 |
| 40 | Nitromethane | 5 mL | 52.7 | 2.9 | 140,000 | 2.4 | 133 | 5 |
| 41 | N,N-Dimethylformamide | 10 mL | 63.6 | 3.5 | 140,000 | 2.4 | 133 | 5 |
| 42 | Phenol | 10 g | 112.7 | 6.2 | 202,000 | 3.3 | 134 | 9 |
| 43 | Triethylamine | 10 mL | 5.5 | 0.3 | 28,200 | 2.6 | 129 | 22 |

[a]All polymerizations reactions were carried out with 55 mg of catalyst in toluene (90 mL) at 80–90 psig of ethylene with temperature control.
[b]Total number of $C_1 + C_2 + C_3 + C_4$ and higher branches per 1000 carbons.

TABLE 7

Polymerization of Ethylene with Various Ni (II) Salicylaldimine Catalysts.[a]

| Sample | Catalyst | Catalyst [mM] | Additive | Additive Amount | Catalyst Productivity (kg PE/mol Ni) | Yield PE (g) | $M_w$ | PDI | $T_m$ (° C.) | Total Branches[b] |
|---|---|---|---|---|---|---|---|---|---|---|
| 44 | I | 0.71 | $Et_2O$ | 10 mL | 720.0 | 46.8 | 197,000 | 3.5 | 134 | 5 |
| 45 | I | 0.71 | DME | 10 mL | 224.6 | 14.6[e] | 27,600 | 7.0 | 118 | 42 |
| 46 | I | 0.71 | DME | 10 mL | 695.4 | 45.2 | 208,000 | 2.3 | 133 | 8 |
| 47 | D | 0.94 | $Et_2O$ | 10 mL | 14.5 | 0.8 | 11,400 | 1.8 | 95 | 42[d] |
| 48 | B | 0.81 | $Et_2O$ | 10 mL | 85.5 | 8.2 | 68,000 | 4.7 | 120 | 26 |
| 49 | F | 0.82 | $Et_2O$ | 10 mL | 265.5 | 14.6 | 161,000 | 6.8 | 128 | 18 |
| 50 | J[c] | 0.65 | $Et_2O$[c] | 10 mL | 469.1 | 25.8 | 72,300 | 5.7 | 119 | 19 |
| 51 | C | 0.71 | $Et_2O$[c] | 10 mL | 472.7 | 26.0 | 257,000 | 2.4 | 131 | 5 |
| 52 | C | 0.71 | DME[c] | 5 mL | 420.0 | 23.1 | 85,000 | 3.2 | 123 | 16 |
| 53 | G[c] | 0.60 | $Et_2O$ | 5 mL | 473.7 | 18.2 | 315,000 | 3.6 | 135.5 | 6 |
| 54 | E[c] | 0.73 | $Et_2O$ | 10 mL | 388.4 | 25.4 | 194,000 | 5.9 | 129.1 | 12 |

[a]All polymerization reactions were carried out in toluene (90 mL) at 80–90 psig of ethylene with temperature control.
[b]Total number of $C_1 + C_2 + C_3 + C_4$ and higher branches per 1000 carbons.
[c]More toluene added during the reaction.
[d]Olefinic species detected by NMR.
[e]Reaction at 45° C.

The data in the above Table 7 indicate that the subject catalysts are active catalysts for the polymerization of ethylene in the presence of Lewis base.

The data in this Table 8 reveal that the subject catalyst can also copolymerize a polar olefinic monomer, such as functionalized norbornene.

TABLE 8

Copolymerization of Ethylene and Functionalized Cyclic Olefins with Catalyst A and Diethyl Ether Additive.

| Sample | Comonomer | Amount of Comonomer | Catalyst loading | Yield PE (g) | $M_w$ | % Incorporation |
|---|---|---|---|---|---|---|
| 48[a] | 5-NAc[c] | 2 mL | 100 mg | 6.0 | | 3.8 wt % |
| 49[b] | 5-NAlc[d] | 2 g | 55 mg | 1.0 | 17,200 | 22.8 wt % |

[a]Polymerization was carried out with 55 mg Catalyst A and 20 ml diethyl ether in toluene (100 mL) at 50 psig of ethylene at 40° C.
[b]Polymerization was carried out with 55 mg Catalyst A and 10 ml diethyl ether in toluene (90 mL) at 40 psig of ethylene at room temperature.
[c]5-NAc is 5-norbornen-2-yl acetate.
[d]5-NAlc is 5-norbornen-2-ol.

TABLE 9

Comparative Ethylene Polymerizations at Elevated Pressure Between Present Catalyst and Nickel Based Catalyst, SHOP.[a,b]

| Sample | Catalyst | Catalyst Concentration (mM) | Yield PE (g) | TON[c] (kg PE/mol cat*hr) | Catalyst Productivity (kg PE/mol Ni) | $M_w$ | PDI | $T_m$ (° C.) | Total Branches |
|---|---|---|---|---|---|---|---|---|---|
| 50 | A | 0.516[c] | 60 | 930 | 546 | 132,000 | 18 | 130.1 | 19 |
| 51 | A | 0.129 | 77 | 1200 | 698 | 65,000 | 9.4 | 125.0 | 28 |
| 52 | A | 0.064 | 64 | 660 | 1156 | 73,800 | 6.4 | 122.6 | 28 |
| 53 | A | 0.029 | 61.0 | 350 | 2440 | 324,000 | 2.3 | 132.8 | 11 |
| 54 | A | 0.129 | 103 | | 805[d] | 85,000 | 9.8 | 124.1 | 24 |
| 55 | A | 0.129 | 153 | 402 | 1187[d] | 190,000 | 11.7 | 127.0 | 15 |
| 56 | A | 0.033 | 78[f] | 1178 | 2356[d] | 347,000 | 3.0 | 136.1 | 5 |
| 57 | SHOP | 0.129 | 4 | 15.5 | 44 | 2,000 | 1.4 | broad ~112 | 17 |
| 58 | SHOP | 0.129 | 11.1 | | 86[d,e] | 2,600 | 1.5 | 120.7 | 12[g] |

[a]Polymerization reactions were carried out in a steel bomb with 1000 mL benzene and 100 mL $Et_2O$ at 500 psig of ethylene without temperature control.
[b]SHOP is a commercially available catalyst (see U.S. 4,716,205 for details of catalyst).
[c]TON is turn over number which is measure of catalyst activity as a rate per hour.
[d]No ether additive used in the polymerization reaction.
[e]Reaction run with temperature control.
[f]Ethylene pressure was 350 psig.
[g]Some olefinic species detected.

Table 9 reveals that catalyst activity is generally enhanced at higher ethylene pressure. The Table also compares the activity of a subject catalyst with the SHOP catalyst. The activity of the subject catalyst is significantly higher (as much as $10^2$ times greater) and the polymer produced has lower branching and higher molecular weight than observed with polymerizations using the SHOP catalyst, with or without Lewis base additive. Table 9 further indicates that polyethylene yield was highest without the Lewis base present.

EXAMPLE LI

The appropriate amount of Na salt of the product of Example XIII and bis(triphenylphosphine)nickel(phenyl) chloride were weighed into a 12 oz. Fisher Porter pressure bottle under an atmosphere of $N_2$ in a dry box. The solvent (90 mL of toluene) was then cannula transferred into the pressure bottle under a positive pressure of ethylene. The ethylene pressure was raised and maintained between 85 and 100 psig. Temperature control was accomplished by a water bath. Stirring of the reaction mixture was maintained by a magnetic stirrer and a stir bar. When the viscosity of the reaction mixture increased to the point where ethylene consumption slowed significantly, the pressure was released and additional amounts of solvent were added. Subsequently, the mixture was repressurized with ethylene. After completion of the polymerization reaction, methanol (1000 mL) and 1 N hydrochloric acid (50 mL) was added to the toluene solution to precipitate the polymer. The polyethylene was collected by filtration through a glass frit, washed with methanol (100 mL) and dried in vacuum. The yield of polyethylene was 38.3 g. Catalyst productivity corresponded to 578 kg PE/mol Ni. The weight average molecular weight and polydispersity of the polymer was 348,000 and 2.2, respectively. The peak melting point was 136.5° C. as determined by DSC.

The results of this polymerization demonstrate that the catalyst of the present invention can be prepared in situ by mixing compound V and a source of nickel atom $\{R^6(L)_2MY\}$.

What is claimed is:

1. A process for forming a polyolefin comprising contacting at least one olefinic compound with a catalyst composition comprising a compound represented by the general formula:

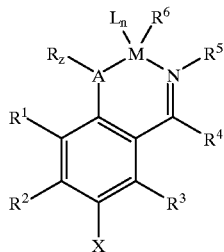

(I)

wherein

R independently represents hydrogen atom; $C_1$–$C_{11}$ alkyl; aryl; or substituted aryl, provided that R represents at least one hydrogen atom, and z is 0 when A is oxygen or sulfur or z is 1 when A is nitrogen;

$R^1$ represents a hydrogen atom; $C_1$–$C_{11}$ alkyl; aryl; substituted aryl wherein the substitution group is selected from $C_1$–$C_4$ alkyl, perfluoroalkyl, nitro, sulfonate or halo group; arylalkyl; siloxyl ((—OSi$E_3$) where E is selected from phenyl or $C_1$–$C_4$ alkyl); nitro group; sulfonate group; halo atom; or a hydrocarbyl terminated oxyhydrocarbylene group (—(BO)$_z$R$^7$) wherein each B independently is selected from a $C_1$–$C_4$ alkylene or an arylene group, O represents oxygen, $R^7$ represents a $C_1$–$C_{11}$ hydrocarbyl group and z is an integer of 1 to 4);

$R^2$ represents hydrogen atom, aryl, substituted aryl, $C_1$–$C_{11}$ alkyl, halogen atom or $R^1$ and $R^2$, together, provide a hydrocarbylene or substituted hydrocarbylene which forms an aromatic or non-aromatic carbocyclic ring;

$R^3$ represents hydrogen;

$R^4$ represents hydrogen atom, a $C_1$–$C_{11}$ alkyl; an aryl; substituted aryl group; or $R^3$ or $R^4$, together, provide a hydrocarbylene or substituted hydrocarbylene forming a non-aromatic carbocyclic ring;

$R^5$ represents a $C_1$–$C_{11}$ alkyl; cycloalkyl; aryl group; a substituted aryl having one or both ortho positions of the aromatic group substituted with a $C_1$–$C_4$ alkyl, the para position (with respect to the N—$R^5$ bond) substituted with a hydrogen, nitro, trifluoromethyl, halogen, methoxy, $C_1$–$C_4$ alkyl, sulfonate or fused or unfused aryl group; or a hydrocarbyl terminated oxyhydrocarbylene group (—(BO)$_2$R$^7$); or $R^1$ and $R^5$ together form an oxyhydrocarbylene chain, —(BO)$_m$B—, wherein each B is independently selected from a $C_1$–$C_4$ alkylene group or an arylene group and m is an integer of 1–4;

n represents an integer of 0 or 1;

$R^6$ represents, when n is 1, an unsubstituted or substituted aromatic group; a $C_1$–$C_{11}$ alkyl; a hydrogen atom or halogen atom or when, n is 0, $R^6$ represents an allyl group or substituted allyl group;

L represents a coordination ligand selected from triphenylphosphine, tri($C_1$–$C_6$ alkyl) phosphine, tricycloalkyl phosphine, diphenyl alkyl phosphine, dialkyl phenylphosphine, triphenoxyphosphine, trialkylamine, $C_2$–$C_{20}$ alkene, substituted $C_2$–$C_4$ alkene, $C_1$–$C_4$ alkoxy, pyridine, di($C_1$–$C_3$ alkyl)ether, tetrahydrofuran, or a nitrile;

X represents a hydrogen atom or an electron withdrawing group selected from $NO_2$, halo, sulfonate ($SO_3^-$), sulfonyl ester ($SO_2R$), carboxyl ($COO^-$), a perfluoroalkyl, or a carboxylic ester group;

M represents a Group VIII transition metal selected from Fe, Co, Ni, Ru, Rh, Pd, Os, Ir, Pt in the +2 oxidation state; and A represents oxygen, nitrogen or sulfur;

in combination with a Lewis base selected from ethers, esters, aldehydes, ketones, alcohols, amides, organocarbonates, organotin compounds, water and mixtures thereof.

2. The process of claim 1 wherein the catalyst composition further comprises a phosphine sponge.

3. The process of claim 1 wherein $R^6$ represents halogen atom and the composition further comprises a catalyst adjunct selected from a partially hydrolyzed aluminum alkyl compound or an aluminum alkyl compound or mixtures thereof.

4. The process of claim 3 wherein the catalyst composition further comprises an adjunct selected from methyl aluminoxane or trialkylaluminum, or mixtures thereof.

5. The process of claim 1 wherein $R^1$ is selected from an aryl group, substituted aryl group or $C_3$–$C_6$ alkyl group.

6. The process of claim 2 or 3 wherein $R^1$ is selected from an aryl group, substituted aryl group or $C_3-C_6$ alkyl group.

7. The process of claim 5 wherein $R^5$ is selected from an aryl group having one or both ortho positions substituted with a $C_1-C_4$ alkyl group.

8. The process of claim 6 wherein $R^5$ is selected from an aryl group having one or both ortho positions substituted with a $C_1-C_4$ alkyl group.

9. The process of claim 5 wherein $R^5$ is selected from an alkyl or cycloalkyl group.

10. The process of claim 6 wherein $R^5$ is selected from an alkyl or cycloalkyl group.

11. The process of claim 2 wherein X is selected from a nitro group, perfluoroalkyl group, sulfonate group or halo atom.

12. The process of claim 3 wherein X is selected from a nitro group, perfluoroalkyl group, sulfonate group or halo atom.

13. The process of claim 1, 2, 3, 4 or 5 wherein M is nickel or palladium atom.

14. The process of claim 1, 2, or 3 wherein the olefinic compound is selected from a $C_2-C_3$ olefinic compound.

15. The process of claim 14 wherein the olefinic compound is ethylene.

16. The process of claim 14 wherein the olefinic compound comprise $C_2-C_3$ olefin and at least one functionalized olefin.

17. The process of claim 16 wherein the functionalized olefin is selected from a carboxylic acid of the formula $CH_2=CH(CH_2)_m COOH$, carboxylic acid ester of the formula $CH_2=CH(CH_2)_m CO_2R^7$ or $CH_2=CHOCOR^7$, an alkyl vinyl ether of the formula $CH_2=CH(CH_2)_m OR^7$, vinyl ketones of the formula $CH_2=CH(CH_2)_m C(O)R^7$, vinyl alcohol of the formula $CH_2=CH(CH_2)_m OH$, wherein m is an integer of 0 to 10 and $R^7$ is a $C_1-C_{10}$ hydrocarbyl, aryl or substituted aryl group; vinylamines of the formula $CH_2=CH(CH_2)_m NR^8_2$ wherein each $R^8$ is independently selected from hydrogen atom or $C_1-C_{11}$ alkyl or aryl; a cycloolefin having a functional group selected from an ester, carboxylic acid, halogen atom, hydroxyl group, or amine group; unsaturated dicarboxylic acid anhydride; carbon monoxide; vinyl halide; or mixtures thereof.

18. The process of claim 1 wherein the catalyst composition comprises a Lewis base selected from ethers, esters, aldehydes, ketones, alcohols, amides, organocarbonates and organonitro compounds and mixtures thereof.

19. The process of claim 1 wherein said Lewis base comprises water present in a molar ratio of water to catalyst compound (I) of from 0 to $10^2$.

20. The process of claim 18 wherein the Lewis base is an ether selected from a di($C_1-C_{18}$ alkyl)ether, aryl ethers, aryl alkyl ethers, cyclic ethers, polyethers, or mixtures thereof.

21. The process of claim 20 wherein the polymerization is carried out in solution and the polymerization solvent comprises an ether or polyether.

22. The process of claim 18 wherein the Lewis base is an organic ester represented by the formula:

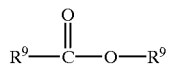

wherein each $R^9$ independently represents a $C_1-C_{11}$ alkyl group.

23. The process of claim 18 wherein the Lewis base is an aldehyde or ketone represented by the formula:

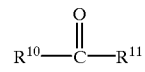

wherein $R^{10}$ represents an unsubstituted or substituted $C_1-C_{12}$ hydrocarbyl group and $R^{11}$ represents a hydrogen atom or an $R^{10}$ group.

24. The process of claim 18 wherein the Lewis base is a monohydric or polyhydric alcohol, said alcohol having hydrocarbyl group composed of a $C_1-C_{12}$ alkyl, aryl, alkaryl or aralkyl group.

25. The process of claim 18 wherein the Lewis base is an amide represented by the formula:

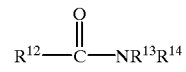

wherein $R^{12}$ and $R^{13}$ each independently represents a $C_1-C_{11}$ hydrocarbyl and $R^{14}$ represents hydrogen or a $C_1-C_{11}$ hydrocarbyl group.

26. The process of claim 18 wherein the Lewis base is an organonitro compound selected from $C_1-C_{11}$ nitroalkanes, $C_1-C_{11}$ polynitro alkanes, and mononitroaromatics.

27. The process of claim 18, 20, 22, 23, 24, 25 or 26 wherein the Lewis base is present in a molar ratio of Lewis base to catalyst compound I from about $10^0$ to about $10^4$.

28. The process of claim 1 wherein $R^1$ is selected from a hydrocarbyl terminated oxyhydrocarbylene group represented by the formula $-(BO)_z R^7$ wherein each B is independently selected from a $C_1-C_4$ alkylene or an arylene group, O is oxygen, $R^7$ is a $C_1-C_{11}$ hydrocarbyl and z is 1–4.

29. The process of claim 1 wherein $R^5$ is selected from an aryl group substituted with a hydrocarbyl terminated oxyalkylene group represented by the formula $-(BO)_z R^7$ wherein B is a $C_1-C_4$ alkylene, O is oxygen, $R^7$ is a $C_1-C_{11}$ hydrocarbyl and z is 1–4.

30. The process of claim 1 wherein $R^5$ is selected from a 2,6-di($C_1-C_4$ alkyl)phenyl and $R^1$ is anthracenyl.

31. The process of claim 1 wherein $R^5$ is selected from a 2,6-di($C_1-C_4$ alkyl)phenyl and $R^1$ is phenanthracenyl.

32. The process of claim 1 wherein $R^5$ is selected from a 2,6-di($C_1-C_4$ alkyl)phenyl and $R^1$ is phenyl.

33. The process of claim 1 wherein $R^1$ and $R^5$ together represent an oxyhydrocarbylene group.

34. The process of claim 2, 3, 4, 5, 7, 9, 11 or 12 wherein the catalyst composition further comprises a Lewis base selected from ethers, esters, aldehydes, ketones, alcohols, amides, organocarbonates, organonitro compounds and mixtures thereof.

35. A process for forming a polyolefin comprising contacting at least one olefinic compound with a catalyst composition comprising:

(A) a compound represented by the formula:

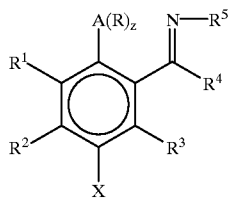

(IV)

wherein
- R independently represents hydrogen atom, $C_1$–$C_{11}$ alkyl, aryl or substituted aryl provided that R represents at least one hydrogen atom, and z is 1 when A is oxygen or sulfur, or z is 2 when A is nitrogen;
- $R^1$ represents a hydrogen atom, $C_1$–$C_{11}$ alkyl; aryl; substituted aryl wherein the substitution group is selected from C1–C4 alkyl, perflouroalkyl, nitro, sulfonate or halo group; arylalkyl; or siloxyl (—OSiE$_3$ wherein E is selected from phenyl or $C_1$–$C_4$ alkyl); nitro group; sulfonate group or halo atom;
- $R^2$ represents hydrogen atom, aryl, substituted aryl, $C_1$–$C_{11}$ alkyl, halogen atom or $R^1$ and $R^2$, together, provide a hydrocarbylene or substituted hydrocarbylene which forms an aromatic or non-aromatic carbocyclic ring;
- $R^3$ represents hydrogen;
- $R^4$ represents hydrogen atom, a $C_1$–$C_{11}$ alkyl; an aryl; substituted aryl group or $R^3$ and $R^4$, together, provide a hydrocarbylene or substituted hydrocarbylene forming a non-aromatic carbocyclic ring;
- $R^5$ represents a $C_1$–$C_{11}$ alkyl; cycloalkyl; aryl group; a substituted aryl having one or both ortho positions of the aromatic group substituted with a $C_1$–$C_4$ alkyl, the para position (with respect to the N—$R^5$ bond) substituted with a hydrogen, nitro, trifluoromethyl, halogen, methoxy or $C_1$–$C_4$ alkyl or fused or unfused aryl or both;
- X represents any electron withdrawing group selected from $NO_2$, halo, sulfonate ($SO_3$), sulfonyl ester ($SO_2R$), carboxyl($COO^-$), a perfluoroalkyl, a carboxylic ester or a hydrogen atom;
- A represents oxygen, nitrogen or sulfur; and (B) a transition metal organic complex, wherein said transition metal is selected from Fe, Co, Ni, Ru, Rh, Pd, Os, Ir or Pt in the +2 valence state;

in combination with
- a Lewis base selected from ethers, esters, aldehydes, ketones, alcohols, amides, organocarbonates, organo-nitro compounds, water and mixtures thereof.

36. The process of claim 35 wherein the transition metal organic complex is a complex of a $C_5$–$C_{10}$ cycloalkyldiene, or a trihydrocarbyl phosphine wherein each hydrocarbyl group is independently selected from $C_1$–$C_{10}$ alkyl, phenyl or cycloalkyl group.

37. The process of claim 36 wherein the complex is a nickel bis-cyclooctadiene.

38. The process of claim 36 wherein the catalyst composition further comprises a phosphine sponge.

39. The process of claim 36 wherein $R^6$ represents halogen atom and the composition further comprises a catalyst adjunct selected from a partially hydrolyzed aluminum alkyl compound or an aluminum alkyl or mxitures thereof.

40. The process of claim 39 wherein the catalyst composition further comprises an adjunct selected from methyl aluminoxane or trialkyl-aluminum or mixtures thereof.

41. The process of claim 36 wherein $R^1$ is selected from aryl group, substituted aryl group or $C_3$–$C_6$ alkyl group.

42. The process of claim 38 or 39 wherein $R^1$ is selected from aryl group, substituted aryl group or $C_3$–$C_6$ alkyl group.

43. The process of claim 41 wherein $R^5$ is selected from an aryl group having one or both ortho positions substituted with a $C_1$–$C_4$ alkyl group.

44. The process of claim 42 wherein $R^5$ is selected from an aryl group having one or both ortho positions substituted with a $C_1$–$C_4$ alkyl group.

45. The process of claim 41 wherein $R^5$ is selected from alkyl or cycloalkyl.

46. The process of claim 42 wherein $R^5$ is selected from alkyl or cycloalkyl.

47. The process of claim 38 wherein X is selected from nitro group, perfluoroalkyl group, sulfonate group or halo atom.

48. The process of claim 39 wherein X is selected from nitro group, perfluoroalkyl group, sulfonate group or halo atom.

49. The process of claim 36, 38, 39, 40 or 41 wherein the transition metal of said complex is selected from nickel or palladium atom.

50. The process of claim 36, 38 or 39 wherein the olefinic compound is a $C_2$–$C_3$ olefinic compound.

51. The process of claim 50 wherein the olefinic compound is ethylene.

52. The process of claim 50 wherein the olefinic compound further comprises at least one functionalized alpha-olefin.

53. The process of claim 52 wherein the functionalized alpha-olefin is selected from carboxylic acid of the formula $CH_2=CH(CH_2)_m COOH$, carboxylic acid ester of the formula $CH_2=CH(CH_2)_m CO_2 R^7$ or $CH_2=CHOCOR^7$, an alkyl vinyl ether of the formula $CH_2=CH(CH_2)_m OR^7$, vinyl ketones of the formula $CH_2=CH(CH_2)_m C(O)R^7$, vinyl alcohol of the formula $CH_2=CH(CH_2)_m OH$, wherein m is an integer of 0 to 10 and $R^7$ is a $C_1$–$C_{10}$ hydrocarbyl, aryl or substituted aryl group; vinylamines of the formula $CH_2=CH(CH_2)_m NR^8{}_2$ wherein each $R^8$ is independently selected from hydrogen atom or $C_1$–$C_{11}$ alkyl or aryl; a cycloolefin having a functional group selected from an ester, carboxylic acid, halogen atom, or amine group; unsaturated dicarboxylic acid anhydride; carbon monoxide; vinyl halide; or mixtures thereof.

54. A process for forming a polyolefin comprising contacting at least one olefinic compound with a catalyst composition comprising:
(i) a compound represented by the formula:

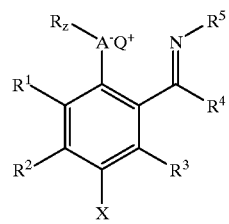

wherein
- R independently represents hydrogen atom, $C_1$–$C_{11}$ alkyl; aryl; or substituted aryl, provided that z is 0 when A is oxygen or sulfur or z is 1 when A is nitrogen;
- $R^1$ represents a hydrogen atom; $C_1$–$C_{11}$ alkyl; aryl; substituted aryl wherein the substitution group is selected from $C_1$–$C_4$ alkyl, perfluoroalkyl, nitro, sulfonate or halo group; arylalkyl; or siloxyl (—$OSiE_3$ wherein E is selected from phenyl or C1–C4 alkyl); nitro group; sulfonate group, halo atom; or a hydrocarbyl terminated oxyhydrocarbylene group, —$(BO)_zR^7$, wherein each B independently is selected from a $C_1$–$C_4$ alkylene or an arylene group, O represents oxygen, $R^7$ represents a $C_1$–$C_{11}$ hydrocarbyl group and z is an integer of 1 to 4;

$R^2$ represents hydrogen atom, aryl, substituted aryl, $C_1$–$C_{11}$ alkyl, halogen atom or $R^1$ and $R^2$, together, provide a hydrocarbylene or substituted hydrocarbylene which forms an aromatic or non-aromatic carbocyclic ring;

$R^3$ represents hydrogen;

$R^4$ represents hydrogen atom, a $C_1$–$C_{11}$ alkyl; an aryl; substituted aryl group; or $R^3$ and $R^4$, together, provide a hydrocarbylene or substituted hydrocarbylene forming a non-aromatic carbocyclic ring;

$R^5$ represents a $C_1$–$C_{11}$ alkyl; cycloalkyl; aryl group; substituted aryl having one or both ortho positions of the aromatic group substituted with a $C_1$–$C_4$ alkyl, the para position (with respect to the N—$R^5$ bond) substituted with a hydrogen, nitro, trifluoromethyl, halogen, methoxy, $C_1$–$C_4$ alkyl, sulfonate or fused or unfused aryl group; or a hydrocarbyl terminated oxyhydrocarbylene chain, —$(BO)_zR^7$; or $R^1$ and $R^5$ together form an oxyhydrocarbylene chain —$(BO)_M$B— wherein each B is independently selected from a $C_1$–$C_4$ alkylene group or an arylene group and m is an integer of 1–4;

X represents any electron withdrawing group selected from $NO_2$, halo, sulfonate ($SO_3^-$), sulfonyl ester ($SO_2R$), carbonyl ($COO^-$), a perfluoroalkyl, a carboxylic ester or a hydrogen atom;

A represents oxygen, nitrogen or sulfur;

Q represents alkali metal cation selected from sodium, potassium or lithium; and (ii) a transition metal organic complex wherein said transition metal is selected from Fe, Co, Ni, Ru, Rh, Pd, Os, Ir or Pt in the +2 valence state;

in combination with a Lewis base selected from ethers, esters, aldehydes, ketones, alcohols, amides, organocarbonates, organonitro compounds, water and mixtures thereof.

55. The process of claim 54 wherein the transition metal organic complex is a complex of formula $R^6(L)_2MY$ wherein $R^6$ represents an unsubstituted or substituted aromatic group; a $C_1$–$C_{11}$ alkyl; an allyl or substituted allyl group;

L represents a coordination ligand selected from triphenylphosphine, tri($C_1$–$C_6$ alkyl)phosphine, tricylcoalkyl phosphine, diphenyl alkyl phosphine, dialkyl phenylphosphine, triphenoxyphosphine, trialkylamine, pyridine, $C_2$–$C_{20}$ alkene, substituted $C_2$–$C_4$ alkene, $C_1$–$C_4$ alkoxy, di($C_1$–$C_3$ alkyl)ether, tetrahydrofuran, or a nitrile;

Y represents a halogen atom selected from chloro, bromo or fluoro; and

M represents a transition metal selected from a Group VIII metal of Fe, Co, Ni, Ru, Rh, Pd, Os, Ir or Pt.

56. The process of claim 55 wherein the complex is bis-triphenylphosphine nickel(phenyl)chloride.

57. The process of claim 55 wherein the catalyst composition further comprises a phosphine sponge.

58. The process of claim 55 wherein $R^6$ represents halogen atom and the composition further comprises a catalyst adjunct selected from a partially hydrolyzed aluminum alkyl compound or an aluminum alkyl or mixtures thereof.

59. The process of claim 58 wherein the catalyst composition further comprises an adjunct selected from methyl alumoxane or trialkylaluminum or mixtures thereof.

60. The process of claim 55 wherein $R^1$ is selected from an aryl group, substituted aryl group or $C_3$–$C_6$ alkyl group.

61. The process of claim 57 or 58 wherein $R^1$ is selected from an aryl group, substituted aryl group or $C_3$–$C_6$ alkyl group.

62. The process of claim 60 wherein $R^5$ is selected from an aryl group having one or both ortho positions substituted with a $C_1$–$C_4$ alkyl group.

63. The process of claim 61 wherein $R^5$ is selected from an aryl group having one or both ortho positions substituted with a $C_1$–$C_4$ alkyl group.

64. The process of claim 60 wherein $R^5$ is selected from alkyl or cycloalkyl.

65. The process of claim 61 wherein $R^5$ is selected from alkyl or cycloalkyl.

66. The process of claim 57 wherein X is selected from a nitro group, perfluoroalkyl group, sulfonate group or halogen atom.

67. The process of claim 58 wherein X is selected from a nitro group, perfluoroalkyl group, sulfonate group or halogen atom.

68. The process of claim 55, 57, 58, 59 or 60 wherein the transition metal of said complex is selected from nickel or palladium atom.

69. The process of claim 55, 57, 58, 59 or 60 wherein the olefinic compound is a $C_2$–$C_3$ olefinic compound.

70. The process of claim 69 wherein the olefinic compound is ethylene.

71. The process of claim 69 wherein the olefinic compound further comprises at least one functionalized olefin.

72. The process of claim 71 wherein the functionalized olefin is selected from a carboxylic acid of the formula $CH_2=CH(CH_2)_mCOOH$, carboxylic acid ester of the formula $CH_2=CH(CH_2)_mCO_2R^7$ or $CH_2=CHOCOR^7$, an alkyl vinyl ether of the formula $CH_2=CH(CH_2)_mOR^7$, vinyl ketones of the formula $CH_2=CH(CH_2)_mC(O)R^7$, vinyl alcohol of the formula $CH_2=CH(CH_2)_mOH$, wherein m is an integer of 0 to 10 and $R^7$ is a $C_1$–$C_{10}$ hydrocarbyl, aryl or substituted aryl group; vinylamines of the formula $CH_2=CH(CH_2)_mNR^8_2$ wherein each $R^8$ is independently selected from hydrogen atom or $C_1$–$C_{11}$ alkyl or aryl; a cycloolefin having a functional group selected from an ester, carboxylic acid, halogen atom, hydroxyl group, or amine group; unsaturated dicarboxylic acid anhydride; carbon monoxide; vinyl halide; or mixtures thereof.

73. The process of claim 71 wherein the functionalized olefin is a hydroxyl substituted or ester substituted norbornene.

74. The process of claim 54 wherein the catalyst composition further comprises a phosphine sponge.

75. The process of claim 54 wherein the catalyst composition comprises Lewis base selected from ethers, esters, aldehydes, ketones, alcohols, amides, organocarbonates and organonitro compounds and mixtures thereof.

76. The process of claim 54, 55, 56, 57, 58, 59, 60, 61, 62, 64, 66 or 67 wherein the catalyst is used in the presence of water and the molar ratio of water to catalyst is from 0 to about $10^2$.

77. The process of claim 75 wherein the Lewis base is an ether selected from di($C_1$–$C_{18}$ alkyl)ethers, aryl ethers, aryl alkyl ethers, cyclic ethers, polyethers, or mixtures thereof.

78. The process of claim 77 wherein the polymerization is carried out in solution and the polymerization solvent comprises an ether or polyether.

79. The process of claim 75 wherein the Lewis base is an organic ester represented by the formula:

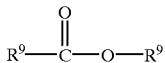

wherein each $R^9$ independently represents a $C_1$–$C_{11}$ alkyl group.

80. The process of claim 75 wherein the Lewis base is an aldehyde or ketone represented by the formula:

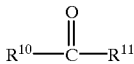

wherein $R^{10}$ represents an unsubstituted or substituted $C_1$–$C12$ hydrocarbyl group and $R^{11}$ represents a hydrogen atom or a $R^{10}$ group.

81. The process of claim 75 wherein the Lewis base is a monohydric or polyhydric alcohol, said alcohol having a hydrocarbyl group composed of a $C_1$–$C_{12}$ alkyl, aryl, alkaryl or aralkyl group.

82. The process of claim 75 wherein the Lewis base is an amide represented by the formula:

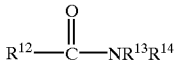

wherein $R^{12}$ and $R^{13}$ each independently represents a $C_1$–$C_{11}$ hydrocarbyl and $R^{14}$ represents hydrogen or a $C_1$–$C_{11}$ hydrocarbyl.

83. The process of claim 75 wherein the Lewis base is an organonitro compound selected from $C_1$–$C_{11}$ nitroalkanes, $C_1$–$C_{11}$ polynitro alkanes, and mono-nitroaromatics.

84. The process of claim 75, 77, 79, 80, 81, 82 or 83 wherein the Lewis base is present in a molar ratio of Lewis base to compound V from about $10^0$ to about $10^4$.

85. The process of claim 54 wherein $R^1$ is selected from a hydrocarbyl terminated oxyhydrocarbylene group represented by the formula —$(BO)_zR^7$ wherein each B is independently selected from a $C_1$–$C_4$ alkylene or an arylene, O is oxygen, $R^7$ is a $C_1$–$C_{11}$ hydrocarbyl and z is 1–4.

86. The process of claim 54 wherein $R^5$ is selected from an aryl group substituted with a hydrocarbyl terminated oxyalkylene group represented by the formula —$(BO)_zR^7$ wherein B is a $C_1$–$C_4$ alkylene, O is oxygen, $R^7$ is a $C_1$–$C_{11}$ hydrocarbyl and z is 1–4.

87. The process of claim 54 wherein $R^5$ is selected from a 2,6-di($C_1$–$C_4$ alkyl)phenyl and $R^1$ is anthracenyl.

88. The process of claim 54 wherein $R^5$ is selected from a 2,6-di($C_1$–$C_4$ alkyl)phenyl and $R^1$ is phenanthracenyl.

89. The process of claim 54 wherein $R^5$ is selected from a 2,6-di($C_1$–$C_4$ alkyl)phenyl and $R^1$ is phenyl.

90. The process of claim 54 wherein $R^1$ and $R^5$ together represent a polyoxyhydrocarbylene group.

91. The process of claim 55, 56, 57, 58, 59, 60, 62, 64, 66 or 67 wherein the catalyst composition comprises a Lewis base selected from ethers, esters, aldehydes, ketones, alcohols, amides, organocarbonates, organonitro compounds and mixtures thereof.

92. The process of claim 1, 2, 3, 4, 5, 7, 9, 11, 12, 18, 19, 20, 21, 22, 23, 24, 25, 26, 28, 29, 30, 31, 32 or 33 wherein said compound is supported on a porous, solid material.

93. The process of claim 6 wherein said compound is supported on a porous solid material.

94. The process of claim 8 wherein said compound is supported on a porous solid material.

95. The process of claim 10 wherein said compound is supported on a porous solid material.

96. The process of claim 13 wherein said compound is supported on a porous solid material.

97. The process of claim 14 wherein said compound is supported on a porous solid material.

98. The process of claim 16 wherein said compound is supported on a porous solid material.

99. The process of claim 17 wherein said compound is supported on a porous solid material.

100. The process of claim 27 wherein said compound is supported on a porous solid material.

101. The process of claim 34 wherein said compound is supported on a porous solid material.

102. The process of claim 54 wherein said catalyst composition further comprises a porous solid catalyst support material.

103. The process of claim 58 wherein said catalyst composition further comprises a porous solid catalyst support material.

104. The process of claim 59 wherein said catalyst composition further comprises a porous solid catalyst support material.

105. The process of claim 74 wherein said catalyst composition further comprises a porous solid catalyst support material.

106. The process of claim 75 wherein said catalyst composition further comprises a porous solid catalyst support material.

107. The process of claim 1, 35 or 54 wherein $R^5$ is selected from aryl, substituted aryl, alkyl or cycloalkyl.

108. The process of claim 5, 41 or 60 where $R^5$ is selected from aryl or substituted aryl.

109. The process of claim 1, 35 or 54 wherein X is selected from nitro group, perfluoroalkyl group, sulfonate group, or halo atom.

110. The process of claim 1, 35 or 54 wherein $R^1$ is selected from t-butyl, anthracenyl, 10-nitroanthracenyl, phenanthracenyl or terphenyl.

111. The process of claim 1, 35 or 54 wherein $R^5$ is 2,6-di($C_1$–$C_4$ alkyl)phenyl group.

112. The process of claim 110 wherein $R^5$ is 2,6-di-(isopropyl)phenyl.

113. The process of claim 1, 35 or 54 wherein X is selected from nitro, sulfonate or perfluoromethyl.

114. The process of claim 1 or 54 wherein R' is selected from a hydrocarbyl terminated oxyhydrocarbylene group represented by the formula —$(BO_zR^7)$ wherein B is independently selected form a $C_1$–$C_4$ alkylene or arylene, O is oxygen, $R^7$ is a $C_1$–$C_{11}$ hydrocarbyl and z is 1–4.

115. The process of claim 1 or 54 wherein $R^5$ is selected from a hydrocarbyl terminated oxyhydrocarbylene group represented by the formula —$(BO_zR^7$ wherein B is independently selected from a $C_1$–$C_4$ alkylene or arylene, O is oxygen, $R^7$ is a $C_1$–$C_{11}$ hydrocarbyl and z is 1–4.

116. The process of claim 35 wherein $R^5$ is selected from a 2,6-di($C_1$–$C_4$ alkyl)phenyl and $R^1$ is phenanthracenyl.

117. The process of claim 1 or 54 wherein $R^1$ and $R^5$ together represent a polyoxyhydrocarbylene group.

118. The process of claim 28, 29, 30 or 116 wherein $R^5$ is a 2,6-di($C_1$–$C_4$ alkyl)-4-nitrophenyl group.

119. The process of claim 117 wherein X is selected from nitro group.

120. The process of claim 28 wherein X is selected from nitro group, perfluoroalkyl group, sulfonate group, or halo atom.

121. The process of claim 1 wherein
$R^1$ is anthracenyl;
$R^2$, $R^3$ and $R^4$ are each hydrogen;
$R^5$ is 2,6-di(isopropyl)phenyl;
$R^6$ is phenyl;
L is triphenyl phosphine;
M is selected from nickel or palladium;
A is oxygen; and
X is hydrogen.

122. The process of claim 1 wherein
$R^1$ is phenanthracenyl;
$R^2$, $R^3$ and $R^4$ are each hydrogen;
$R^5$ is 2,6-di(isopropyl)phenyl;
$R^6$ is phenyl;
L is triphenyl phosphine;
M is selected from nickel or palladium;
A is oxygen; and
X is hydrogen.

123. The process of claim 1 wherein
$R^1$ is phenyl;
$R^2$, $R^3$ and $R^4$ are each hydrogen;
$R^5$ is 2,6-di(isopropyl)phenyl;
$R^6$ is phenyl;
L is triphenyl phosphine;
M is selected from nickel or palladium;
A is oxygen; and
X is hydrogen.

124. The process of claim 1 wherein
$R^1$ is anthracenyl;
$R^2$, $R^3$ and $R^4$ are each hydrogen;
$R^5$ is 2,6-di(isopropyl)-4-nitrophenyl;
$R^6$ is phenyl;
L is triphenyl phosphine;
M is selected from nickel or palladium;
A is oxygen; and
X is hydrogen.

125. The process of claim 1 wherein
$R^1$ is 10-nitroanthracenyl;
$R^2$, $R^3$ and $R^4$ are each hydrogen;
$R^5$ is 2,6-di(isopropyl)phenyl;
$R^6$ is phenyl;
L is triphenyl phosphine;
M is selected from nickel or palladium;
A is oxygen; and
X is nitro.

126. The process of claim 1 wherein
$R^1$ is phenyl;
$R^2$, $R^3$ and $R^4$ are each hydrogen;
$R^5$ is 2,6-di(isopropyl)phenyl;
$R^6$ is phenyl;
L is triphenyl phosphine;
M is selected from nickel or palladium;
A is oxygen; and
X is nitro.

127. The process of claim 1 wherein
$R^1$ is 10-nitroanthracenyl;
$R^2$, $R^3$ and $R^4$ are each hydrogen;
$R^5$ is 2,6-di(isopropyl)-4-nitrophenyl;
$R^6$ is phenyl;
L is triphenyl phosphine;
M is selected from nickel or palladium;
A is oxygen; and
X is nitro.

128. The process of claim 1 wherein
$R^1$ is phenanthracenyl;
$R^2$, $R^3$ and $R^4$ are each hydrogen;
$R^5$ is 2,6-di(isopropyl)phenyl;
$R^6$ is phenyl;
L is triphenyl phosphine;
M is selected from nickel or palladium;
A is oxygen; and
X is nitro.

129. The process of claim 1 wherein
$R^1$ is 10-nitroanthracenyl;
$R^2$, $R^3$ and $R^4$ are each hydrogen;
$R^5$ is 2,6-di(isopropyl)phenyl;
$R^6$ is phenyl;
L is triphenyl phosphine;
M is selected from nickel or palladium;
A is oxygen; and
X is hydrogen.

130. The process of claim 1 wherein
$R^1$ is terphenyl;
$R^2$, $R^3$ and $R^4$ are each hydrogen;
$R^5$ is 2,6-di(isopropyl)phenyl;
$R^6$ is phenyl;
L is triphenyl phosphine;
M is selected from nickel or palladium;
A is oxygen; and
X is hydrogen.

131. The process of claim 1 wherein
$R^1$ is terphenyl;
$R^2$, $R^3$ and $R^4$ are each hydrogen;
$R^5$ is 2,6-di(isopropyl)-4-nitrophenyl;
$R^6$ is phenyl;
L is triphenyl phosphine;
M is selected from nickel or palladium;
A is oxygen; and
X is hydrogen.

132. The process of claim 1 wherein
$R^1$ is terphenyl;
$R^2$, $R^3$ and $R^4$ are each hydrogen;
$R^5$ is 2,6-di(isopropyl)phenyl;
$R^6$ is phenyl;
L is triphenyl phosphine;
M is selected from nickel or palladium;
A is oxygen; and
X is nitro.

133. The process of claim 1 wherein
$R^1$ is terphenyl;
$R^2$, $R^3$ and $R^4$ are each hydrogen;
$R^5$ is 2,6-di(isopropyl)-4-nitrophenyl;

$R^6$ is phenyl;
L is triphenyl phosphine;
M is selected from nickel or palladium;
A is oxygen; and
X is nitro.

134. The process of claim 1 wherein
$R^1$ is 10-nitroanthracenyl;
$R^2$, $R^3$ and $R^4$ are each hydrogen;
$R^5$ is 2,6-di(isopropyl)phenyl;
$R^6$ is phenyl;
L is triphenyl phosphine;
M is selected from nickel or palladium;
A is oxygen; and
X is nitro.

135. The process of claim 1 wherein
$R^1$ is phenyl;
$R^2$, $R^3$ and $R^4$ are each hydrogen;
$R^5$ is 2,6-di(isopropyl)-4-nitrophenyl;
$R^6$ is phenyl;
L is triphenyl phosphine;
M is selected from nickel or palladium;
A is oxygen; and
X is hydrogen.

136. The process of claim 1 wherein
$R^1$ is phenyl;
$R^2$, $R^3$ and $R^4$ are each hydrogen;
$R^5$ is 2,6-di(isopropyl)-4-nitrophenyl;
$R^6$ is phenyl;
L is triphenyl phosphine;
M is selected from nickel or palladium;
A is oxygen; and
X is nitro.

137. The process of claim 35 or 54 wherein
$R^1$ is anthracenyl;
$R^2$, $R^3$ and $R^4$ are each hydrogen;
$R^5$ is 2,6-di(isopropyl)phenyl;
A is oxygen;
X is hydrogen; and
the transition metal of the transition metal organic complex is selected from nickel or palladium.

138. The process of claim 35 or 54 wherein
$R^1$ is phenanthracenyl;
$R^2$, $R^3$ and $R^4$ are each hydrogen;
$R^5$ is 2,6-di(isopropyl)phenyl;
A is oxygen;
X is hydrogen; and
the transition metal of the transition metal organic complex is selected from nickel or palladium.

139. The process of claim 35 or 54 wherein
$R^1$ is phenyl;
$R^2$, $R^3$ and $R^4$ are each hydrogen;
$R^5$ is 2,6-di(isopropyl)phenyl;
A is oxygen;
X is hydrogen; and
the transition metal of the transition metal organic complex is selected from nickel or palladium.

140. The process of claim 35 or 54 wherein
$R^1$ is anthracenyl;
$R^2$, $R^3$ and $R^4$ are each hydrogen;
$R^5$ is 2,6-di(isopropyl)-4-nitrophenyl;
A is oxygen;
X is hydrogen; and
the transition metal of the transition metal organic complex is selected from nickel or palladium.

141. The process of claim 35 or 54 wherein
$R^1$ is 10-nitroanthracenyl;
$R^2$, $R^3$ and $R^4$ are each hydrogen;
$R^5$ is 2,6-di(isopropyl)phenyl;
A is oxygen;
X is nitro; and
the transition metal of the transition metal organic complex is selected from nickel or palladium.

142. The process of claim 35 or 54 wherein
$R^1$ is phenyl;
$R^2$, $R^3$ and $R^4$ are each hydrogen;
$R^5$ is 2,6-di(isopropyl)phenyl;
A is oxygen;
X is nitro; and
the transition metal of the transition metal organic complex is selected from nickel or palladium.

143. The process of claim 35 or 54 wherein
$R^1$ is 10-nitroanthracenyl;
$R^2$, $R^3$ and $R^4$ are each hydrogen;
$R^5$ is 2,6-di(isopropyl)-4-nitrophenyl;
A is oxygen;
X is nitro; and
the transition metal of the transition metal organic complex is selected from nickel or palladium.

144. The process of claim 35 or 54 wherein
$R^1$ is phenanthracenyl;
$R^2$, $R^3$ and $R^4$ are each hydrogen;
$R^5$ is 2,6-di(isopropyl)phenyl;
A is oxygen;
X is nitro; and
the transition metal of the transition metal organic complex is selected from nickel or palladium.

145. The process of claim 35 or 54 wherein
$R^1$ is 10-nitroanthracenyl;
$R^2$, $R^3$ and $R^4$ are each hydrogen;
$R^5$ is 2,6-di(isopropyl)phenyl;
A is oxygen;
X is hydrogen; and
the transition metal of the transition metal organic complex is selected from nickel or palladium.

146. The process of claim 35 or 54 wherein
$R^1$ is terphenyl;
$R^2$, $R^3$ and $R^4$ are each hydrogen;
$R^5$ is 2,6-di(isopropyl)phenyl;
A is oxygen;
X is hydrogen; and
the transition metal of the transition metal organic complex is selected from nickel or palladium.

147. The process of claim 35 or 54 wherein
$R^1$ is terphenyl;
$R^2$, $R^3$ and $R^4$ are each hydrogen;
$R^5$ is 2,6-di(isopropyl)-4-nitrophenyl;
A is oxygen;

X is hydrogen; and the transition metal of the transition metal organic complex is selected from nickel or palladium.

148. The process of claim 35 or 54 wherein $R^1$ is terphenyl;

$R^2$, $R^3$ and $R^4$ are each hydrogen;

$R^5$ is 2,6-di(isopropyl)phenyl;

A is oxygen;

X is nitro; and the transition metal of the transition metal organic complex is selected from nickel or palladium.

149. The process of claim 35 or 54 wherein $R^1$ is terphenyl;

$R^2$, $R^3$ and $R^4$ are each hydrogen;

$R^5$ is 2,6-di(isopropyl)-4-nitrophenyl;

A is oxygen;

X is nitro; and the transition metal of the transition metal organic complex is selected from nickel or palladium.

150. The process of claim 35 or 54 wherein $R^1$ is phenyl;

$R^2$, $R^3$ and $R^4$ are each hydrogen;

$R^5$ is 2,6-di(isopropyl)-4-nitrophenyl;

A is oxygen;

X is hydrogen; and the transition metal of the transition metal organic complex is selected from nickel or palladium.

151. The process of claim 1, 2, 3, 4, 5, 7, 9, 11 or 12 wherein M is selected from the group consisting of Fe, Co, Ni or Pd.

152. The process of claim 6 wherein M is selected from the group consisting of Fe, Co, Ni or Pd.

153. The process of claim 15 wherein M is selected from the group consisting of Fe, Co, Ni or Pd.

154. The process of claim 16 wherein M is selected from the group consisting of Fe, Co, Ni or Pd.

155. The process of claim 18 wherein M is selected from the group consisting of Fe, Co, Ni or Pd.

156. The process of claim 19 wherein M is selected from the group consisting of Fe, Co, Ni or Pd.

157. The process of claim 35, 36, 38, 39, 40 or 41 wherein M is selected from the group consisting of Fe, Co, Ni, or Pd.

158. The process of claim 51 wherein M is selected from the group consisting of Fe, Co, Ni or Pd.

159. The process of claim 52 wherein M is selected from the group consisting of Fe, Co, Ni or Pd.

160. The process of claim 54, 55, 56, 57, 58, 59, 60, 62, 64, 66 or 67 wherein M is selected from the group consisting of Fe, Co, Ni or Pd.

* * * * *